United States Patent
Hochberg

(10) Patent No.: US 6,476,012 B2
(45) Date of Patent: Nov. 5, 2002

(54) ESTRADIOL-16α-CARBOXYLIC ACID ESTERS AS LOCALLY ACTIVE ESTROGENS

(75) Inventor: Richard B. Hochberg, Guilford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 10/056,635

(22) Filed: Jan. 23, 2002

(65) Prior Publication Data

US 2002/0143002 A1 Oct. 3, 2002

Related U.S. Application Data

(60) Provisional application No. 60/264,157, filed on Jan. 25, 2001.

(51) Int. Cl.[7] .......................... A61K 31/56; A61K 31/59; C07J 1/00
(52) U.S. Cl. ...................... 514/182; 514/169; 552/623; 552/625; 552/629
(58) Field of Search ................. 552/623, 625, 552/629; 514/169, 182

(56) References Cited

U.S. PATENT DOCUMENTS

| | | | | |
|---|---|---|---|---|
| 3,045,012 A | * | 7/1962 | Waukegan | 260/239.57 |
| 3,190,895 A | * | 6/1965 | Waukegan | 260/397.1 |
| 3,287,356 A | * | 11/1966 | Arth | 260/239.55 |

FOREIGN PATENT DOCUMENTS

DE 864257 * 1/1953

OTHER PUBLICATIONS

Donald Poirier et al. (Molecular and Cellular Endocrinology, 171 (2001), 119–128).*
Inhofffen, Hans H. (DN 52:88397, CAPLUS, abstract of DE 864,257).*

* cited by examiner

Primary Examiner—Sabiha Qazi
(74) Attorney, Agent, or Firm—Henry D. Coleman; Coleman Sudol Sapone, P.C.

(57) ABSTRACT

The present invention relates to analogs of estradiol, which, in their most preferred embodiment, act as locally active estrogens without significant systemic action. A series of 16α-carboxylic acid substituted steroids and their esters is presented which exhibit excellent biological activity for use in pharmaceutical compositions for the treatment of symptomology associated with menopause. The present invention is therefore directed to compounds according to the structure:

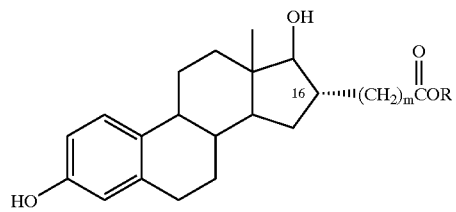

Where R is H, a $C_1$ to $C_5$ alkyl, vinyl, $CF_3$, $CH_2CH_2F$, $CH_2CHF_2$ or $CH_2CF_3$; and m is from 0–2, or a pharmaceutically acceptable salt thereof. Preferably, R is methyl, ethyl, propyl, iso-propyl, butyl, iso-butyl, pentyl, neo-pentyl, vinyl, $CF_3$, $CH_2CH_2F$, $CH_2CHF_2$ or $CH_2CF_3$ and m is 0. More preferably, R is methyl, ethyl, $CH_2CH_2F$, $CH_2CHF_2$ or $CH_2CF_3$ and m is 0.

29 Claims, 7 Drawing Sheets

Scheme 1

Scheme 2

Scheme 3

ESTRADIOL-16α-CARBOXYLIC ACID ESTERS AS LOCALLY ACTIVE ESTROGENS

RELATED APPLICATIONS

This application claims the benefit of priority from U.S. provisional application No. 60/264,157, filed Jan. 25, 2001.

FIELD OF THE INVENTION

The present invention relates to novel 16-α estradiol ester compounds and their use as locally active estrogens in the treatment of the symptomology of menopause.

BACKGROUND OF THE INVENTION

It is well recognized that pharmacologic estrogen administration (hormone replacement therapy, HRT) can alleviate most, if not all, of the symptomology associated with the menopause. These symptoms include, but are not limited to: bone loss associated with osteoporosis; heart disease associated with changes in blood lipids and lipoproteins; hot flashes; and vaginal dyspareunia.[1] However, there are risks associated with estrogen administration in HRT as well as oral contraceptive use, and include an association with endometrial cancer, breast cancer, and stroke. Although for the most part, the therapeutic benefits of HRT outweigh the risks, nevertheless, while the risks are small, they do exist.[2-4]

Estrogen therapy, directly and indirectly, affects a number of organs. Some of the outcomes associated with estrogen therapy are deleterious. Consequently, where possible, symptomology which could be ameliorated by local rather than systemic administration could limit the adverse side-effects of estrogen therapy. One such syndrome that can be treated directly, caused by estrogen deprivation or estrogen antagonists, is vaginal dyspareunia. It is a common disorder which affects a large proportion of women, approximately 40% within 10 years of the onset of the menopause.[5] It is and important factor in the quality of life for women so afflicted, as it is associated with a severe physical and psychological impact. It is not only painful but it can dramatically influence a women's self image and lead to clinical depression.[6] Another possible use of local estrogens includes topical administration to aging skin. The skin contains ER and it is an estrogen target organ.[11-13] While topical application of estrogens to the vaginal mucosa has been used to treat vaginal dyspareunia of the menopause, these estrogens are adsorbed into the blood and result in significant blood levels of estrogens.[7-10] Thus, this therapy may not be used where systemic estrogens are contraindicated.

Since topically applied estrogen is adsorbed into the blood, its purpose is defeated. A potent estrogen whose range is limited to the tissue to which it is applied would be ideal for the treatment of these disorders. Similar therapeutic agents with locally limited actions have been termed "soft drugs"[14], compounds which have a limited region of activity due to rapid metabolic inactivation. Ester groups have been used to convey "soft drug" properties to biologically active molecules because hydrolytic enzymes, including esterases, are ubiquitously distributed.[15] The ester containing compounds are the active agents while their hydrolysis products, the carboxylic acids, are inactive. In this manner, locally active glucocorticoids have been developed as antiinflammatory agents for the skin. These are esters of steroids substituted with a carboxylic acid group. The parent carboxylic acids do not bind to the glucocorticoid receptor and are biologically inert while their corresponding esters bind to the glucocorticoid receptor with high affinity.[16,17] The esters are rapidly hydrolyzed to the parent steroidal-carboxylic acid and thus, are inactivated by the ubiquitous esterases. Consequently, they can be used as antiinflammatory agents for skin because their action is localized to the area to which they were applied, i.e., their rapid inactivation prevents systemic action.[18]

Similarly, in a study designed to produce affinity chromatographic supports for the purification of the estrogen receptor (ER) it was found that carboxylic acid analogs of estradiol ($E_2$) at C-7α- and C-17α are very poor ligands if they bind at all, but the methyl esters of these same analogs have much improved affinity for the ER.[19] It appears from those results that a charged carboxylic acid group in proximity to the steroid ring interferes with binding to the ER and that masking the charge by esterification reverses this interference.

OBJECTS OF THE INVENTION

It is an object of the invention to provide novel compounds and pharmaceutical compositions for use in treating the symptomology of menopause.

It is an additional object of the invention to provide prodrug forms of estrogen which may be used to provide a therapeutic effect while limiting deleterious effects which may occur with systemic administration of estrogenic steroids.

It is yet another object of the invention to provide methods for treating the symptomology of menopause, especially including vaginal dyspareunia.

It is still another object of the invention to provide topical dosage forms of the present compounds, and in particular, vaginal creams, gels and lotions for use in the treatment of certain symptoms associated with menopause, especially vaginal dyspareunia.

Controls were injected with vehicle. The next morning, 2,3,5-triphenyltetrazolium chloride was instilled in the vagina and thirty minutes later the animals were killed and the vaginal reductase activity was determined spectrophotometrically Panel a: the steroids were dissolved in 10 μL of 25% propylene glycol in saline. Panel b: the steroids were dissolved in 10 μL of sesame oil. n=5. Error bars are±S.D. *$P<0.001$ compared to the control.

Figure 4:
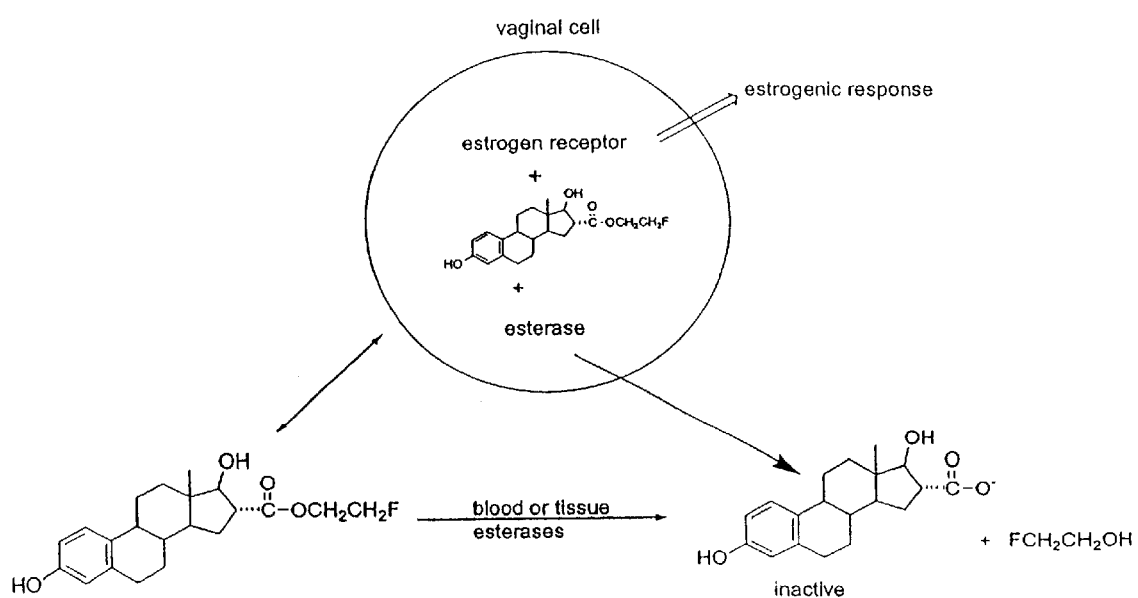

FIG. 4 depicts the estrogenic action and biological inactivation of E16-1,2$F_1$ 16. Locally administered compound 16 diffuses into the vaginal cell where it binds to the estrogen receptor and produces an estrogenic stimulus. Esterases in the vagina or within other tissues and blood rapidly hydrolyze 16 to 2'-fluoroethanol and the biologically inert alkyl carboxylate E16-1,0, 8. Consequently, estrogenic stimulation is confined to the area of administration.

Figure 5:
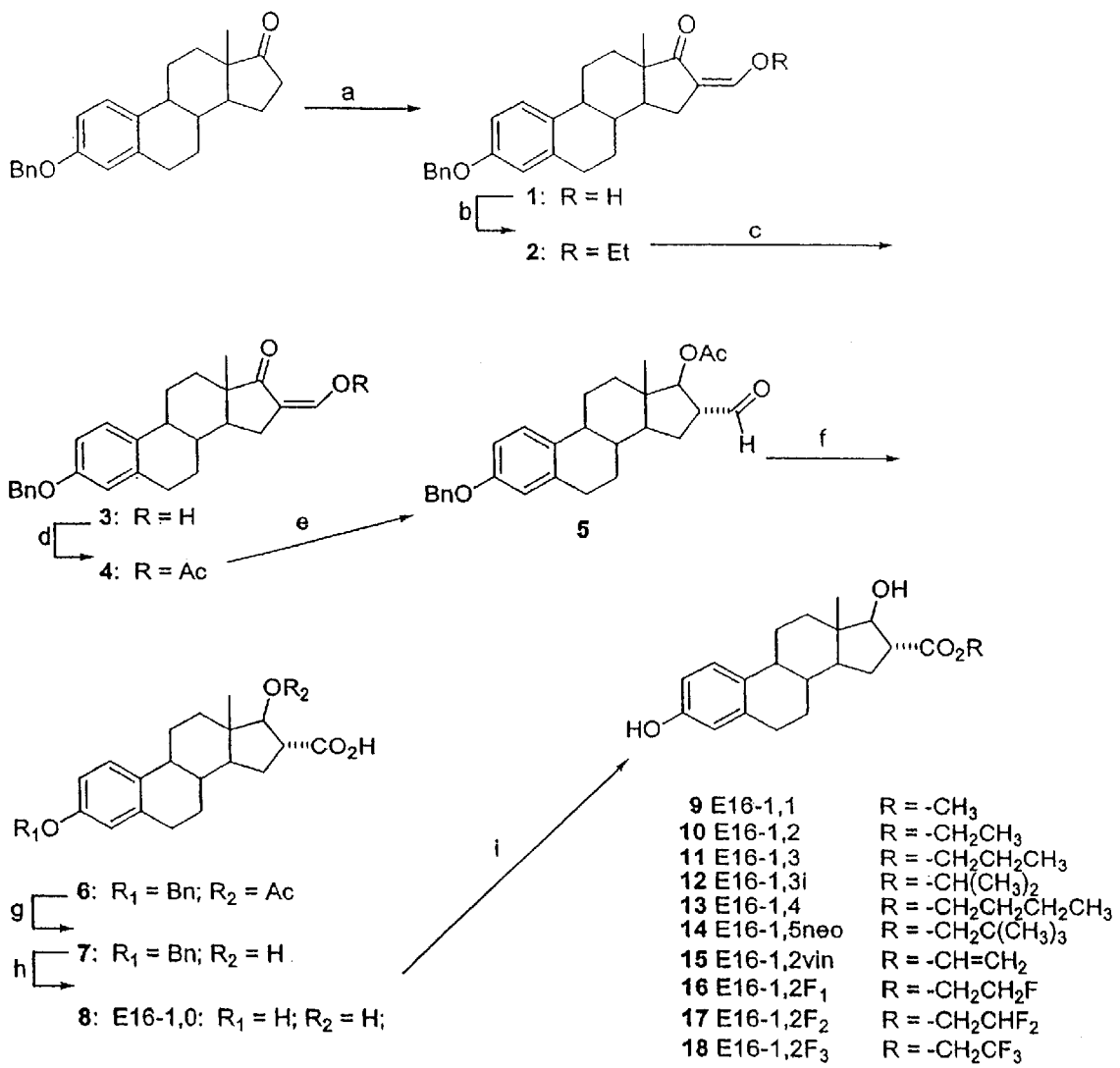

FIG. 5, Scheme 1 shows the chemical synthesis of 16α-formyl ester analogs and individual chemical steps and reagents used to effect those steps: (a) NaH, THF; Ethyl formate (estrone-3-benzyl ether→1); (b) $K_2CO_3$, EtI, acetone (1→2); (c) $LiAlH_4$, $Et_2O$ (2→3); (d) $Ac_2O$, Pyridine (3→4); (e) 10% aqueous HCl, THF (4→5); (f) Jones oxidation (5→6); (g) KOH-MeOH, 50° C. (6→7); (h) 5% Pd—$C/H_2$, EtOH (7→8); (i) ROH, $SOCl_2$ or ROH, pTsOH or vinyl propionate, $PdCl_2$—LiCl, MeOH (8→9–18)

Figure 6:
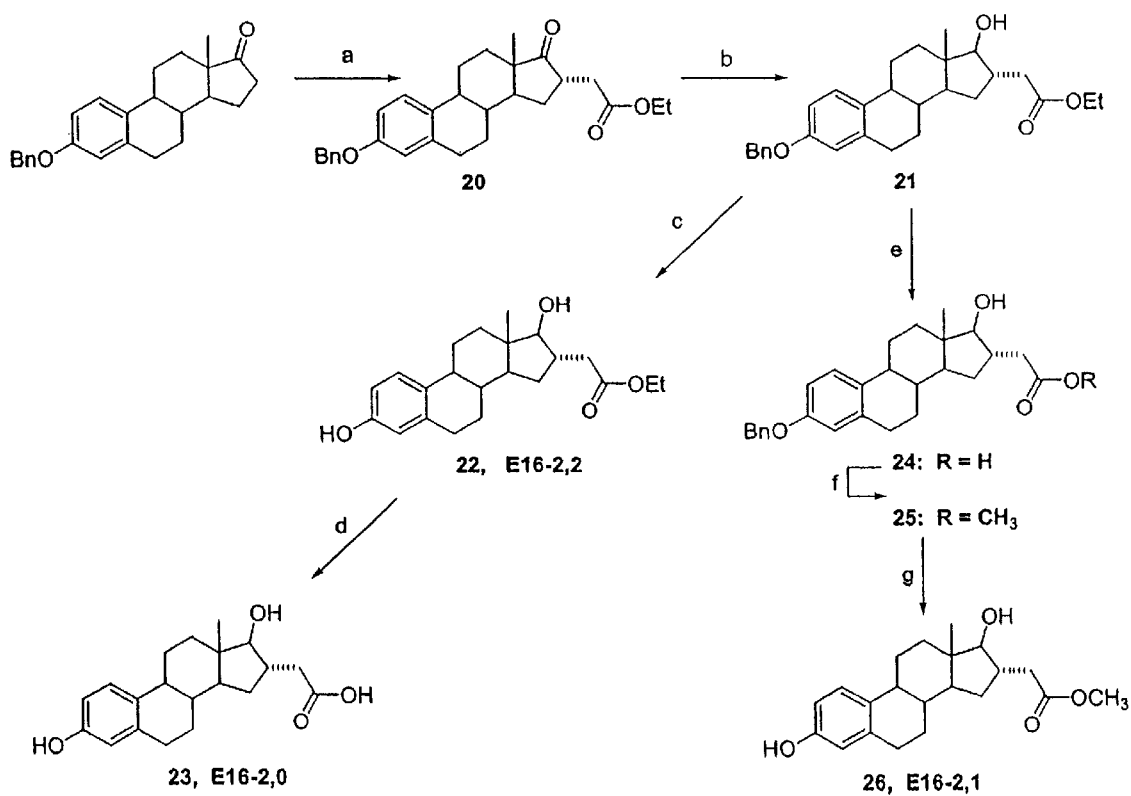

FIG. 6, Scheme 2 shows the chemical synthesis of 16α-acetyl ester analogs and individual chemical steps and reagents used to effect those steps: (a) LDA, THF; Ethyl bromoacetate (estrone-3-benzyl ether→20); (b) Li(OtBu)$_3$AlH, THF (20→21); (c) 5% Pd—$C/H_2$, EtOH (21→22); (d) 5% KOH-MeOH (22→23); (e) 5% KOH-MeOH (21→24); (f) MeOH, $SOCl_2$ (24→25); (g) 5% Pd—$C/H_2$ (25→26)

Figure 7:
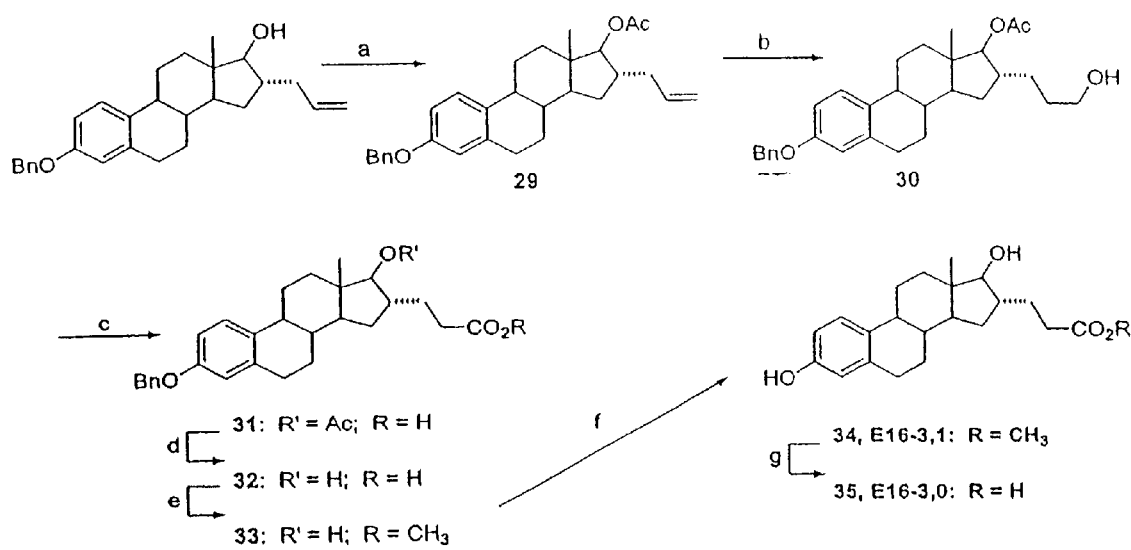

FIG. 7, Scheme 3 shows the chemical synthesis of 16α-propionate ester analogs and individual chemical steps and reagents used to effect those steps: (a) $AcO_2$, pyridine (16α-allyl-3-benzylestrone→29); (b) $BH_3$-THF; $Et_3NO$, diglyme, 150° C. (29→30); (c) Jones oxidation (30→31); (d) KOH-MeOH, 55° C. (31→32); (e) MeOH, $SOCl_2$ (32→33); (f) 5% Pd—$C/H_2$, EtOH (33→34); (g) KOH-MeOH, 60° C. (34→35)

SUMMARY OF THE INVENTION

The present invention is directed to compounds according to the structure:

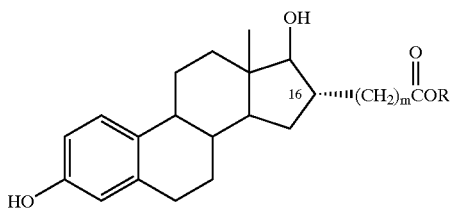

Where R is H, a $C_1$ to $C_5$ alkyl, vinyl, $CF_3$, $CH_2CH_2F$, $CH_2CHF_2$ and $CH_2CF_3$; and m is from 0–2. Preferably, R is H, methyl, ethyl, propyl, iso-propyl, butyl, iso-butyl, pentyl, neo-pentyl, vinyl, $CF_3$, $CH_2CH_2F$, $CH_2CHF_2$ and $CH_2CF_3$. Preferably, m is 0 and R is methyl, ethyl, $CH_2CH_2F$, $CH_2CHF_2$ or $CH_2CF_3$. More preferably, m is 0 and R is methyl, ethyl, $CH_2CH_2F$ or $CH_2CHF_2$.

The present invention also relates to pharmaceutical compositions according to the present invention comprising an effective amount of at least one compound as described above in combination with a pharmaceutically acceptable carrier, additive or excipient. Preferably, pharmaceutical compositions according to the present invention are formulated in topical dosage form, more preferably as vaginal creams, gels or suppositories for local delivery of the active compounds to the patient.

In another aspect of the present invention, a therapeutic treatment comprises administering one or more of the active compounds according to the present invention to a patient in need of therapy for the treatment of the symptomology associated with menopause. Preferred aspects of the present invention include the treatment of vaginal dyspareunia in patients in need of such therapy, especially in patients for which systemic estrogens are contraindicated, comprising topically administering to the vaginal area of such a patient an effective amount of one or more active compound according to the present invention in pharmaceutical dosage form (preferably, as a vaginal gel, cream, lotion or suppository).

DETAILED DESCRIPTION OF THE INVENTION

The following terms shall be used throughout the specification to describe the present invention.

The term "patient" is used throughout the specification to describe an animal, preferably a human, to whom treatment, including prophylactic treatment, with the compounds according to the present invention is provided. For treatment of the symptomology, conditions or disease states which are specific for a specific animal such as a human patient, the term patient refers to that specific animal. In most instances in the present invention, the patient is a human female exhibiting symptomology associated with menopause.

The term "effective amount" is used throughout the specification to describe concentrations or amounts of compounds according to the present invention which may be used to produce a favorable change in the symptomology, disease or condition treated, whether that change is a decrease in or reversal of the effects of symptomology or disease state depending upon the disease state or condition treated. In the present invention, in preferred aspects, an effective amount is that amount which is used to treat the symptomology associated with menopause, in its most preferred aspect, vaginal dyspareunia. An effective amount for purposes of treating one or more disease states or symptoms of the present invention, includes the timing and manner in which an active compound is administered to a patient.

The term "alkyl" is used throughout the specification to describe a hydrocarbon radical containing between one and five carbon units. Alkyl groups for use in the present invention include linear or branched-chain groups such as methyl, ethyl, propyl, i-propyl, butyl, sec-butyl, tert-butyl, pentyl, neo-pentyl, etc.

The term "menopause" is used throughout the specification to describe the period in a woman's life between the ages of approximately 45 and 50 after which menstruation (menses) naturally ceases. The symptomology associated with menopause which is particularly relevant to the present invention includes bone loss associated with osteoporosis and most importantly, vaginal dyspareunia.

The term "vaginal dyspareunia" is used throughout the specification to describe a symptom or condition of menopause wherein vaginal atrophy, dryness and pain during sexual intercourse occurs.

A preferred therapeutic aspect according to the present invention relates to methods for treating the symptomology of menopause comprising administering therapeutically effective amounts or concentrations of one or more of the compounds according to the present invention to treat the symptomology associated with menopause in the patient. This symptomology preferably includes bone loss associated with osteoporosis and vaginal dyspareunia. In each of these cases, local delivery of compounds according to the present invention may take maximum advantage of the local effects of the compounds in vivo.

Pharmaceutical compositions based upon these novel chemical compounds comprise the above-described compounds in a therapeutically effective amount for the treatment of the symptomology of menopause or a related condition or disease state, optionally in combination with a pharmaceutically acceptable additive, carrier or excipient. Pharmaceutical compositions in topical dosage form for local delivery of the active compounds, especially vaginal creams, gels and lotions, are particularly preferred.

Certain of the compounds, in pharmaceutical dosage form, may be used as prophylactic agents for preventing or reducing the likelihood of a patient exhibiting specific symptomology associated with menopause.

Modifications of the active compound can affect the solubility, bioavailability and rate of metabolism of the active species, thus providing control over the delivery of the active species. Further, the modifications may affect the activity of the compound, in some cases increasing.the activity over the parent compound. This can easily be assessed by preparing the derivative and testing its activity according to known methods well within the routineer's skill in the art.

The compounds of this invention may be incorporated into formulations for all routes of administration including for example, oral and parenteral including intravenous, intramuscular, intraperitoneal, intrabuccal, transdermal and in suppository form. Topical dosage forms and in particular, creams, lotions, gels and suppositories which can be delivered to the vaginal membranes are particularly preferred for use in the present invention.

Pharmaceutical compositions based upon these novel chemical compounds comprise the above-described compounds in a therapeutically effective amount for treating the symptomology of menopause which have been described hereinabove, especially including vaginal dyspareunia, optionally in combination with a pharmaceutically acceptable additive, carrier and/or excipient. One of ordinary skill in the art will recognize that a therapeutically effective amount of one of more compounds according to the present invention will vary with the condition or symptomology to be treated, its severity, the treatment regimen to be employed, the pharmacokinetics of the agent used, as well as the patient to be treated.

In the pharmaceutical aspect according to the present invention, the compound according to the present invention is formulated preferably in admixture with a pharmaceutically acceptable carrier. In general, it is preferable to administer the pharmaceutical composition in topically administrable form, especially including vaginal creams, gels, lotions and suppositories, but a number of formulations may be administered via a parenteral, intravenous, intramuscular, transdermal, buccal, subcutaneous or other route. Intravenous and intramuscular formulations, when used, are administered in sterile saline. Of course, one of ordinary skill in the art may modify the formulations within the teachings of the specification to provide numerous formulations for a particular route of administration, if desired, without rendering the compositions of the present invention unstable or compromising their therapeutic activity, noting that the ester groups (R) are somewhat labile. In particular, the modification of the present compounds to render them more soluble in water or other vehicle, for example, may be accomplished by minor modifications which are well within the ordinary skill in the art. It is also well within the routineer's skill to modify the route of administration and dosage regimen of a particular compound in order to manage the pharmacokinetics of the present compounds for maximum beneficial effect to the patient.

The amount of compound included within therapeutically active formulations according to the present invention is an effective amount for treating the symptom or condition. In its most preferred embodiments, the present compounds are administered topically (to vaginal membranes) for treating the symptomology of vaginal dyspareunia. In general, a therapeutically effective amount of the presently preferred compound in dosage form usually ranges from slightly less than about 0.001 mg./kg. to about 1.0 g./kg., preferably about 0.01 mg/kg to about 0.1 mg/kg of the patient or considerably more depending upon the compound used, the condition or symptomology treated and the route of administration, although exceptions to this dosage range may be contemplated by the present invention and are well within the teachings of the present invention.

Administration of the active compound preferably occurs via a topical dosage route, and in particular, via a vaginal cream, gel, lotion or vaginal suppository. In certain aspects, administration may range from continuous to oral administration and may include oral, topical, parenteral, intramuscular, intravenous, sub-cutaneous, transdermal (which may include a penetration enhancement agent) and buccal routes of administration, among other routes of administration. Other routes of administration include local delivery at the site of administration, for example, from an implanted material (such as an artificial hip or other prosthesis), among others. Preferably, the active compounds are administered via a topical route, most preferably as vaginal creams, gels, lotions or suppositories for administration to the vaginal membranes or vaginal cavity of the patient.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., topical, oral or parenteral, preferably topical. In preparing pharmaceutical compositions in the preferred topical dosage form, any of the usual pharmaceutical media may be used including thickeners, emollients, emulsifiers, etc. may be used to produce creams, gels, salves, ointments and the like for topical delivery to the vaginal membranes. Administration via a vaginal suppository is also preferably contemplated by the present invention.

In the case of oral dosage forms, liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like maybe used. If desired, the tablets or capsules may be enteric-coated or sustained release by standard techniques.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

The present compounds may be used to treat animals, and in particular, mammals, especially including humans, as patients. Patients may be treated by administering to the patient an effective amount of one or more of the compounds according to the present invention optionally in a pharmaceutically acceptable carrier or diluent, either alone, or in combination with other known pharmaceutical agents, depending upon the condition or symptomology to be treated. This treatment can also be administered in conjunction with other conventional menopausal therapies.

The active compound is included in the pharmaceutically acceptable carrier or diluent in an amount sufficient to deliver to a patient a therapeutically effective amount for the desired indication, without causing toxic effects in the patient treated.

The compound is conveniently administered in any suitable unit dosage form, including but not limited to one containing less than 1 mg (preferably, at least 1 mg) to 3000 mg, preferably 5 to 500 mg of active ingredient per unit dosage form. A topical dosage ranging from about 5 to about 250 mg is usually convenient.

The concentration of active compound in the drug composition will depend on absorption, distribution, inactivation, and excretion rates of the drug as well as other factors known to those of skill in the art. It is to be noted that dosage values will also vary with the severity of the condition or symptomology to be treated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time. In its most preferred aspect of the present invention, i.e., in the topical administration of compounds according to the present invention to the vaginal membranes of the patient to be treated, the active may be administered as infrequently as once every several days to several times a day, depending upon the activity of the compounds and other factors well known in the art.

Oral compositions, if used, will generally include an inert diluent or an edible carrier. They may be enclosed in gelatin capsules (soft or hard) or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The active compound may also be administered as a component of an elixir, suspension, syrup, wafer, chewing gum or the like. A syrup may contain, in addition to the active compounds, sucrose and/or corn syrup as a sweetening agent and certain preservatives, dyes and colorings and flavors.

The active compound can also be mixed with other active materials which do not impair the desired action, or with materials which supplement the desired action, such as other hormonal agents, and in other instances depending upon the desired therapy or target, other pharmaceutically active compounds.

Solutions or suspensions used for parenteral, intradermal, subcutaneous, or topical application can include.the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. If administered intravenously, preferred carriers include, for example, physiological saline or phosphate buffered saline (PBS). In the case of the preferred pharmaceutical compositions in topical dosage forms, creams, gels and/or viscous lotions may be used as vaginal delivery forms. Creams, gels, lotions and suppositories may be formulated using standing pharmaceutical procedures.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid, among others. Methods for preparation of such formulations are well known and will be readily apparent to those skilled in the art.

Liposomal suspensions may also be pharmaceutically acceptable carriers. These may be prepared according to methods known to those skilled in the art. For example, liposome formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

The present invention relates to a family of 16α-carboxylic acid analogs of $E_2$ of varying alkyl chain lengths which were esterified with a number of alcohols of different size and substituents, and performed a structure-activity study in order to determine the feasibility of producing, in its most preferred embodiment, a locally active estrogen. The 16α-position of $E_2$ was chosen for substitution because it is chemically accessible and because some substitutions there are known to be tolerated by the ER.[20] The carboxylic acids and their esters were tested for their affinity for the ER and their ability to activate an estrogen inducible gene in tissue culture. The results were correlated with the relative rate at which the esters are hydrolyzed by hepatic esterase(s). Finally, candidate esters were tested in in vivo bioassays for their systemic and local action.

Synthetic Chemistry

The following describes the general chemical steps which were carried out to provide the compounds according to the present invention. The general synthetic schemes are presented in FIGS. 5, 6 and 7.

Scheme 1, FIG. 5, describes the synthesis of the 16α-formyl ester analogs of estradiol 9–18 employing a methodology used previously by the Katzenellenbogen group to prepare 16α-hydroxymethyl substituted estradiol derivatives.[20] Deprotonation of 3-benzylestrone with NaH in THF followed by acylation with ethyl formate gave the enol ether 1 which was protected with EtI as the ethyl enol ether 2. Stereoselective reduction of the 17-ketone with LiAlH$_4$ gave the 17β-hydroxyl compound 3 that was protected with Ac$_2$O in pyridine to give the acetate 4. Acid hydrolysis of 4 with 10% aqueous HCl produced the 16α-aldehyde 5 as the only isomer. Oxidation with $CrO_3$—$H_2SO_4$ [21] gave the acid 6 which was deprotected with KOH-MeOH followed by hydrogenolysis with 5% Pd—C/$H_2$ to produce the acid 8, E16-1,0.

The methyl, ethyl, propyl, and butyl esters, E16-1,1 9; E16-1,2 10; E16-1,3 11 and E16-1,4 13, were prepared by reacting 8 with the appropriate alcohol in the presence of $SOCl_2$; the isopropyl, neopentyl, monofluoro-, difluoro- and trifluoroethyl esters, E16-1,3i 12; E16-1,5neo 14; E16-1,2$F_1$ 16; E16-1,2$F_2$ 17 and E16-1,2$F_3$, 18 were prepared by reacting 8 with the appropriate alcohol in the presence of pTsOH. The vinyl ester, E16-1,2 vin 15, was prepared from 8 through a vinyl exchange reaction with vinyl propionate and $PdCl_2$—LiCl as catalyst.[22] In the $^1H$ NMR spectra of all these esters, the signal for H-17α appears at about δ 3.90 ppm with a coupling constant ($J_{17\alpha,16}$) of 7.4–9 Hz indicating that these esters have the same stereochemistry at C-16. Proof of the stereochemistry at C-16 was obtained by reduction of E16-1,2 with $LiAlH_4$, a reagent known not to affect epimerizable asymmetric centers.[23,24] The reduction gives the hydroxymethyl steroid whose $^1H$ NMR spectrum is identical with that of the known 16α-hydroxymethyl estradiol 19, prepared by the literature procedure.[26]

The synthesis of the 16α-acetyl analogs of estradiol 22, 23, 26 is shown in Scheme 2, FIG. 6. Deprotonation of 3-benzylestrone with LDA in THF at 0° C. followed by alkylation with ethyl bromoacetate at <−20° C. gave the ketoester 20 as only the α isomer in 35% yield with 43% recovered starting material. Reduction of the ketone with lithium tri-t-butoxyaluminum hydride at −78° C. in THF gave the 17β-alcohol 21. Deprotection of phenolic hydroxyl group with 5% Pd—C/$H_2$ in EtOH gave the ethyl ester 22, E16-2,2. Saponification of 22 with 5% KOH-MeOH gave the acid 23, E16-2,0. The protected ethyl ester 21 was saponified, and the resulting acid 24 was converted to the methyl ester, 25. Deprotection of 25 with 5% Pd—C/$H_2$ gave the methyl ester 26, E16-2,1. Proof of the stereochemistry at C-16 was obtained by Dibal reduction of ethyl ester 21, followed by Tebbe reaction of the resulting aldehyde 27 to give 16-allyl-3-benzylestradiol 28. The $^1H$ NMR spectrum is identical to the 16α-allyl substituted steroid obtained by the literature method.[25]

The synthesis of the 16α-propionate ester analogs of estradiol 34, 35 is shown in Scheme 3, FIG. 7. The known 16α-allyl-3-benzyloxy)estra-1,3,5(10)-trien-17β-ol[25] was first protected as the acetate with $Ac_2O$ in pyridine. Hydroboration of 29 and oxidation with trimethylamine oxide in diglyme produced the alcohol 30 which was oxidized with $CrO_3$—$H_2SO_4$ to give the acid 31. Saponification of the 17β-acetate with KOH-MeOH followed by esterification of the carboxylic acid with MeOH in the presence of $SOCl_2$ gave 33. Deprotection of the phenolic hydroxyl group with 5% Pd—C/$H_2$ provided 34, E16-3,1. The acid 35, E16-3,0 was obtained by saponification of 34.

The following non-limiting examples are provided to exemplify the present invention. One of ordinary skill will recognize that the presentation of these examples for purposes of exemplary teachings of the present invention and is not be construed as limiting the breadth of the invention in any way.

EXAMPLES

Materials and Methods. $^1H$ NMR spectra were recorded with Bruker AM500 (500 MHz) and chemical shifts are reported relative to residual $CHCl_3$. Purification by flash-chromatography was performed according to the procedure of Still [36] using 230–400 mesh silica gel (EM Science, Darmstadt Germany). High resolution mass spectra were obtained by electrospray ionization on a Micromass Q-Tof spectrometer by Dr. Walter J. McMurray at the Yale University Comprehensive Cancer Center using either PEG as an internal standard with $NH_4OAc$ or NaI as an internal standard. Elemental analyses were performed by Schwarzkopf Micro Analytical Laboratory, Woodside N.Y. The computer program Prism was purchased from GraphPad Software Inc. (San Diego, Calif.). The cell culture reagents were obtained from Gibco-BRL (Grand Island, N.H.). Unless otherwise indicated, solvents (analytical or HPLC grade) and reagents were used as supplied, and all reactions were carried out under nitrogen.

Chromatographic Systems. Thin-layer chromatography (TLC) was performed using Merck silica Gel plates ($F_{254}$) (EM Science) and visualized using phosphomolybdic acid or UV illumination. TLC systems: T-1, hexanes/EtOAc (3:1); T-2, hexanes/EtOAc (2:1); T-3, hexanes/acetone (5:1); T-4, EtOH/EtOAc (1:9); T-5, $CHCl_3$/MeOH (5:1); T-6, hexanes/EtOAc (1:1); T-7, ($CH_2Cl_2$) Analytical high-performance liquid chromatography (HPLC) was performed on a Waters 600E system (Waters Co. Milford Mass.) equipped with a 484 variable wavelength detector. H-1, Protein I-60 column (7.8 mm×30 cm, Waters Co.) with HOAc/iPrOH/$CH_2Cl_2$ (0.1:6:93.9) at 3 ml/min; H-2, Microsorb-MV C18 (5 ☐m, 4.6 mm×25 cm, Varian Analytical Instruments, Walnut Creek Calif.) with HOAc/$CH_3CN$/$H_2O$ (0.13:35:64.87) at 0.8 mL/min; H-3, Protein I-60 column (7.8 mm×30 cm, Waters Co.) with $CH_2Cl_2$ at 3 mL/min; H-4, Microsorb-MV C18 (5 ☐m, 4.6 mm×25 cm, Varian Analytical Instruments) with $CH_3CN$/$H_2O$ (45:55) at 1 mL/min; H-5, Ultrasphere ODS (5 μm 10 mm×25 cm, Altex Scientific Operations Co, Berkeley, Calif.) with $CH_3CN$/$H_2O$ (60:40) at 1.3 mL/min; H-6, Microsorb-MV C18 (5 ☐m, 4.6 mm×25 cm, Varian Analytical Instruments) with $CH_3CN$/$H_2O$ (60/40) at 1 mL/min; H-7, Ultrasphere ODS (5 μm 10 mm×25 cm, Altex Scientific Operations Co.) with $CH_3CN$/$H_2O$ (40/60) at 3 mL/min H-8, Ultrasphere ODS (5 μm 10 mm×25 cm, Altex Scientific Operations Co.) with $H_2O$/$CH_3CN$ (50/50) at 3 mL/min; H-9, Microsorb-MV C18 (5 μm, 4.6 mm×25 cm, Varian Analytical Instruments) with THF/$CH_3CN$/$H_2O$ (5.5:45:49.5) at 0.8 mL/min; H-10, Microsorb-MV C18 (5 μm, 4.6 mm×25 cm, Varian Analytical Instruments) with HOAc/$CH_3CN$/$H_2O$ (0.13:35:64.87) at 1 mL/min; H-11 Ultrasphere ODS (5 μm 10 mm×25 cm, Altex Scientific Operations Co.) with THF/$CH_3CN$/$H_2O$ (5.5:45:49.5) at 1.5 mL/min; H-12 Microsorb-MV C18 (5 μm, 4.6 mm×25 cm, Varian Analytical Instruments) with THF/$CH_3CN$/$H_2O$, (6:40:54) at 0.8 mL/min; H-13, LiChrosorb RP-18, (5 μm, 4.6 mm×25 cm, EM Science) with HOAc/$CH_3CN$/$H_2O$ (0.11:45:54.89) at 1 mL/min; H-14, Protein I-60 column (7.8 mm×30 cm, Waters Co.) with HOAc/iPrOH/$CH_2Cl_2$ (0.2:5:94.8) at 3 mL/min) H-15, Microsorb-MV C18 (5 μm, 4.6 mm×25 cm, Varian Analytical Instruments) with HOAc/$CH_3CN$/$H_2O$ (0.12:40:59.88) at 1 mL/min;.

Chemical Synthesis of Compounds 3-(Benzyloxy-16-(ethoxymethylidene)estra-1,3,5(10)-trien-17-one (2). A solution of 5.08 g (14.1 mmol) of benzylestrone in 20 mL of anhydrous THF was added to a suspension of 2.03 g (42.3 mmol) of a 50% dispersion of NaH in 20 mL of anhydrous THF at 0° C. To this was added 5.7 mL (70 mmol) of ethyl formate and the reaction was stirred at rt for 3 h. The reaction was quenched with saturated aqueous $NH_4Cl$ (50 mL) and extracted with EtOAc (3×, 50 mL). Combined organic extracts were washed with 10% sodium metabisulfite (20 mL), $H_2O$ (20 mL), dried over $Na_2SO_4$ and concentrated in vacuo giving a yellow foam.

A solution of 5.61 g of this crude material, 13.3 g (96.2 mmol) of $K_2CO_3$, 6.62 mL (82.8 mmol) of EtI in acetone (70 mL) was stirred at rt for 48 h. The reaction was poured into $H_2O$ (200 mL) and extracted with $CH_2Cl_2$ (3×, 100 mL). Combined organic extracts were dried over $Na_2SO_4$ and concentrated in vacuo giving an orange oil. Purification by flash chromatography on a 5×18 cm column of silica gel eluting with hexanes/EtOAc (3:1) gave 2.56 g (43%, two steps) of 2. Data for 2: TLC, T-1, $R_f$ 0.27. $^1H$ NMR (500 MHz, $CDCl_3$) δ 0.93 (s, 3H, H-18), 1.35 (t, 3H, J=7.2 Hz, —$CH_2\underline{CH_3}$), 4.05–4.11 (m, 2H, —$\underline{CH_2}CH_3$), 5.04 (s, 2H, benzylic), 6.74 (d, 1H, J=2.2 Hz, H-4), 6.80 (dd, 1H, J=8.7,2.2 Hz, H-2), 7.21 (d, 1H, J=8.7 Hz, H-1), 7.30 (s, 1H, —C=$\underline{CH}$OEt), 7.32–7.44 (m, 5H, Ar—H).

3-Benzyloxy-16-(ethoxymethylidene)estra-1,3,5(10)-trien-17β-ol (3). A solution of 316.4 mg (0.759 mmol) of ketone 2 in 2 mL of $Et_2O$ was stirred at rt as 43 mg (1.14 mmol of $LiAlH_4$ was added. Reaction was stirred at rt for 1.25 h, poured into EtOAc (1 mL) and saturated aqueous Na—K tartrate (30 mL) and extracted with EtOAc (3×, 50 mL). Combined organic extracts were dried over $Na_2SO_4$ and concentrated in vacuo giving a white gel. Purification of the residue by flash chromatography on a 3×21 cm column of silica gel using hexanes/EtOAc (2:1)as eluent gave 194 mg (61%) of 3: TLC, T-2, $R_f$ 0.34.

3-Benzyloxy-16-(ethoxymethylidene)estra-1,3,5(10)-trien-17β-yl acetate (4). A solution of 3 (194 mg), acetic anhydride (1 mL) in pyridine (3ml) was stirred at rt overnight under $N_2$. Reaction was poured into saturated aqueous $NaHCO_3$ (150 mL) and extracted with $CH_2Cl_2$ (3×, 100 mL). Combined organic extracts were dried over $Na_2SO_4$ and concentrated in vacuo. Purification of the residue by flash chromatography on a 2×20 cm column of silica gel using hexanes/EtOAc (4:1) as eluent gave 183 mg (86%) of 4 as a white solid: TLC, T-2, $R_f$ 0.67.

3-Benzyloxy-16α-formylestra-1,3,5(10)-trien-17β-yl acetate (5). A solution of 183 mg (0.397 mmol) of 4 in THF (1.5 mL) with 4 drops of 10% aqueous HCl and 2 drops of $H_2O$ was stirred at rt for 6 h. Reaction was poured into saturated aqueous $NaHCO_3$ (100 mL) and extracted with $CH_2Cl_2$ (3×, 75 mL). Combined organic extracts were dried over $Na_2SO_4$ and concentrated in vacuo. Purification of the residue by repeated (3×) flash chromatography on a 2×15 cm column of silica gel using hexanes/acetone (6:1) as eluent gave 96.9 mg (56%) of 5 as a white solid. Data for 5: TLC, T-3, $R_f$ 0.22. $^1H$ NMR (500 MHz, $CDCl_3$) δ 0.91 (s, 3H, H-18), 2.10 (s, 3H, OAc), 4.86 (d, 1H, J=8.1 Hz, H-17), 5.04 (s, 2H, benzylic), 6.73 (d, 1H, J=2.7 Hz, H-4), 6.79 (dd, 1H, J=8.5, 2.7 Hz, H-2), 7.19 (d, 1H, J=8.5 Hz, H-1), 7.31–7.44 (m, 5H, Ar—H), 9.83 (d, 1H, J=3.1 Hz, O=CH); HRMS (ES) calcd for $C_{28}H_{32}O_4Na$ (M+$Na^+$) m/e 455.2198, found m/e 455.2205.

3-Benzyloxy-17β-acetoxyestra-1,3,5(10)-trien-16α-carboxylic acid (6). A solution of 824 mg (1.90 mmol) of 5 in 120 mL of acetone was cooled to 0° C. and 710 μL of Jones reagent solution (8 M solution of $CrO_3$ in aqueous $H_2SO_4$)[37] was added. The reaction mixture was stirred at 0° C. for 30 min, diluted with MeOH (20 mL) and $H_2O$ (20 mL), concentrated to about 30 mL, and extracted with $CH_2Cl_2$ (3×, 70 mL). Combined organic extracts were dried over $Na_2SO_4$ and concentrated in vacuo. Purification of the residue by flash chromatography on a 2×17 cm column of silica gel using EtOH/$CH_2Cl_2$ (5:95) gave 784.4 mg (92%) of 6 as a white foam. Data for 6: TLC, T-4, $R_f$ 0.78. $^1H$ NMR (500 MHz, $CDCl_3$) δ 0.87 (s, 3H, H-18), 2.10 (s, 3H, OAc), 5.02 (d, 1H, J=7.1 Hz, H-17α), 5.04(s, 2H, benzylic), 6.72 (d, 1H, J=2.8 Hz, H-4), 6.79 (dd, 1H, J=8.5, 2.8 Hz, H-2), 7.20 (d, 1H, J=8.5 Hz, H-1), 7.31–7.44 (m, 5H, Ar—H); HRMS (ES) calcd for $C_{28}H_{32}O_5Na$ (M+$Na^+$) m/e 471.2147, found m/e 471.2146.

3-Benzyloxy-17β-hydroxyestra-1,3,5(10)-trien-16α-carboxylic acid (7). A solution of 784.4 mg (1.75 mmol) of 6, 5% aqueous KOH in MeOH (7 mL) was stirred and heated at 50° C. for 3 h. Reaction was cooled to rt, poured into $H_2O$ (50 mL), adjusted to pH 1 with 10% aqueous HCl, and extracted with EtOAc (3×, 100 mL). Combined organic extracts were washed with $H_2O$ (100 mL), dried over $Na_2SO_4$, and concentrated in vacuo. Purification of the residue by flash chromatography on a 2×17 cm column of silica gel using EtOH/EtOAc (10:90) gave 491.5 mg (69%) of 7 as a white foam. Data for 7: TLC, T-4, $R_f$ 0.63. $^1H$ NMR (500 MHz, $CDCl_3$) δ 0.86 (2, 3H, H-18), 3.94 (d, 1H, J=8.3 Hz, H-17α), 5.04 (s, 2H, benzylic), 6.73 (d, 1H, J=2.2 Hz, H-4), 6.80 (dd, 1H, J=8.7, 2.2 Hz, H-2), 7.21 (d, 1H, J=8.7 Hz, H-1), 7.32–7.45 (m, 5H, Ar—H).

3,17β-dihydroxyestra-1,3,5(10)-trien-16α-carboxylic acid (8) E16-1,0. A solution of 491.5 mg (1.21 mmol) of 7 in 5 mL of EtOH was added to a suspension of 50 mg 5% Pd/C in 10 mL EtOH and reaction was stirred at rt under an atm of $H_2$ for 19 h. Reaction was filtered through a 1" pad of Celite and washed through with EtOH (100 mL). The filtrate was concentrated in vacuo giving 343 mg 89% of 8 as a white solid. Purification of 15.7 mg of this material by HPLC in system H-1 ($R_t$=14 min) gave 12.8 mg of 8 for bioassay. Data for 8: TLC, T-5, $R_f$ 0.38. $^1H$ NMR (500 MHz, DMSO-$d_6$) δ 0.69 (s, 3H, H-18), 3.69 (d, 1H, J=7.5 Hz, H-17α), 4.91 (br s, 1H, OH), 6.42 (d, 1H, 2.3 Hz, H-4), 6.50 (dd, 1H, J=8.3, 2.3 Hz, H-2), 7.03 (d, 1H, J=8.3 Hz, H-1), 8.98 (s, 1H, OH), 11.96 (br s, 1H, OH); HRMS (ES) calcd for $C_{19}H_{28}NO_4$ (M+$NH_4^+$) m/e 334.2018, found m/e 334.2007. HPLC system, H-1, 280 nm, $R_t$=14 min, and system H-2, 280 nm, $R_t$=9 min, >99% pure.

Methyl (3,17β-dihydroxyestra-1,3,5(10)-trien-16α-yl) formate (9, E16-1,1). A solution of 27.9 mg (0.0883 mmol) of carboxylic acid 8, 9.66 μL (0.132 mmol) of $SOCl_2$ in 2 mL of MeOH was stirred and heated at 40° C. for 2.25 h in a 5 mL flask equipped with a reflux condenser. Reaction mixture was poured into saturated aqueous $NaHCO_3$ (50 mL) and extracted with $CH_2Cl_2$ (3×, 50 mL). Combined organic extracts were dried over $Na_2SO_4$ and concentrated in vacuo giving a brown oil. Purification of the residue by flash chromatography on a 2×16 cm column of silica gel using hexanes/EtOAc (1:1) as eluent gave 23.1 mg (79%) of 9 as a white solid. Purification of this material by HPLC in system H-3, 280 nm, gave 17.0 mg of 9 for bioassay. Data for 9: TLC, T-6, $R_f$ 0.325. $^1H$ NMR (500 MHz, $CDCl_3$, $D_2O$) δ 0.84 (s, 3H, H-18), 3.75 (s, 3H, $OCH_3$), 3.89 (dd, 1H, J=7.7 Hz, H-17α), 6.57 (d, 1H, J=2.8 Hz, H-4), 6.63 (dd, 1H, J=8.3, 2.8 Hz, H-2), 7.15 (d, 1H, J=8.3 Hz, H-1); HRMS (ES) calcd for $C_{20}H_{30}NO_4$ (M+$NH_4^+$) m/e 348.2175, found m/e 348.2191. HPLC system, H-3, 280 nm, $R_t$=14 min, and system H-4, 280 nM, $R_t$=8 min, >99% pure.

Ethyl (3,17β-dihydroxyestra-1,3,5(10)-trien-16α-yl) formate (10, E16-1,2). Compound 10 was prepared by esterification of acid 8 (13.5 mg, 0.0427 mmol) with EtOH as described for the preparation of 9. Purification of the residue by flash chromatography on a 1×15 cm column of silica gel using hexanes/EtOAc (1:1) as eluent gave 13.8 mg (94%) of 10 as a white solid. Purification of this material by HPLC, H-3, 280 nm, $R_t$=11 min gave 11 mg of 10 for bioassay. Data for 10: TLC, T-6, $R_f$ 0.46. $^1$H NMR (500 MHz, CDCl$_3$, D$_2$O) δ 0.84(s, 3H, H-18), 1.31 (t, 3H, J=7.1 Hz, OCH$_2$CH$_3$), 3.88 (d, 1H, J=8.0 Hz, H-17α), 4.21 (q, 2H, J=7.1 Hz, OCH$_2$CH$_3$), 6.57 (d, 1H, J=2.8 Hz, H-4), 6.63 (dd, 1H, J=8.4, 2.8 Hz, H-2), 7.15 (d, 1H, J=8.4 Hz, H-1); HRMS (ES) calcd for C$_{21}$H$_{32}$NO$_4$ (M+NH$_4^+$) m/e 362.2331, found m/e 362.2331. Anal. (C$_{21}$H$_{28}$O$_4$) C, H. Carbon found 73.23%, calculated 73.23; Hydrogen found 8.36%, calculated 8.19.

Propyl (3,17β-dihydroxyestra-1,3,5(10)-trien-16α-yl) formate (11, E16-1,3). Compound 11 was prepared by esterification of acid 8 (663 mg, 0.209 mmol) with n-propanol as described for the preparation of 9. Purification of the residue by flash chromatography on a 2×15 cm column of silica gel using hexanes/EtOAc (2:1) as eluent gave 46.2 mg (62%) of 11 as a white solid. Purification of 22 mg of this material by HPLC, H-5, gave 20.4 mg of 11 for bioassay. Data for 11: TLC, T-2, $R_f$=0.41. $^1$H NMR (500 MHz, CDCl$_3$) δ 0.85 (s, 3H, H-18), 0.98 (t, 3H, J=7.6 Hz, CH$_3$), 3.88 (d, 1H, J=7.4 Hz, H-17α), 4.11 (m, 2H, OCH$_2$), 6.57 (d, 1H, J=2.5 Hz, H-4), 6.63 (dd, 1H, J=8.3, 2.5 Hz, H-2), 7.16 (d, 1H, J=8.3 Hz, H-1); HRMS (ES) calcd for C$_{22}$H$_{34}$NO$_4$ (M+NH$_4^+$) m/e 376.3488, found m/e 376.2493. HPLC system, H-3, 280 nm, $R_t$=12 min, and system H-5, 280 nM, $R_t$=9.5 min, >99% pure.

Isopropyl (3,17β-dihydroxyestra-1,3,5(10)-trien-16α-yl) formate (12, E16-1,3i). A solution of 44 mg (0.139 mmol) of acid 8, 10 mg (0.053 mmol) of pTsOH in isopropanol (20 mL) was stirred and heated at 85° C. for 18 h. A Dean-Stark trap filled with 4 Å sieves was added and heating was continued for 18 h. Reaction mixture was allowed to cool to rt, poured into saturated aqueous NaHCO$_3$ (20 mL) and extracted with CH$_2$Cl$_2$ (3×, 50 mL). Combined organic extracts were dried over Na$_2$SO$_4$ and concentrated in vacuo. Purification of the residue by flash chromatography on a 2×15 cm column of silica gel using hexanes/EtOAc (2:1) as eluent gave 21.3 mg (43%) of 12 as a white solid. Purification of this material by HPLC in system H-3, 280 nm, followed by crystallization from acetone/petroleum ether gave 8.4 mg of 12 for bioassay. Data for 12: TLC, T-6, $R_f$ 0.55. $^1$H NMR (500 MHz, CDCl$_3$) δ 0.84 (s, 3H, H-18), 1.28 (d, 3H, J=6.5 Hz, CH$_3$), 1.282 (d, 3H, J=6.5 Hz, CH$_3$), 3.85 (br d, 1H, J=9.3 Hz, H-17α), 5.07 (sept, 1H, J=6.5 Hz, —CH—), 6.57 (d, 1H, J=2.7 Hz, H-4), 6.63 (dd, 1H, J=8.3, 2.7 Hz, H-2), 7.15 (d, 1H, J=8.3 Hz, H-1); HRMS (ES) calcd for C$_{22}$H$_{34}$NO$_4$ (M+NH$_4^+$) m/e 376.2488, found m/e 376.2485. HPLC system, H-3, 280 nm, $R_t$=11 min, and system H-6, 280 nM, $R_t$=7 min, >99% pure.

n-Butyl (3,17β-dihydroxyestra-1,3,5(10)-trien-16α-yl) formate (13, E16-1,4). Compound 13 was prepared by esterification of acid 8 (58.5 mg, 0.185 mmol) with butanol as described for the preparation of 9. Purification of the residue by flash chromatography on a 2×15 cm column of silica gel gave 50 mg (73%) of 13 as a white solid. Data for 13: TLC, T-2, $R_f$ 0.30. $^1$H NMR (500 MHz, CDCl$_3$) δ 0.85 (s, 3H, H-18), 0.96 (t, 3H, J=7.4 Hz, —CH$_3$), 3.87 (d, 1H, J=8.0 Hz, H-17α), 4.15 (m, 2H, OCH$_2$), 6.57 (d, 1H, J=2.7 Hz, H-4), 6.63 (dd, 1H, J=8.4, 2.7 Hz, H-2), 7.15 (d, 1H, J=8.4 Hz, H-1); HRMS (ES) calcd for C$_{23}$H$_{36}$NO$_4$ (M+NH$_4^+$) m/e 390.2644, found m/e 390.2647. HPLC system H-3, 280 nm, $R_t$=11 min, and system H-6, 280 nM, $R_t$=9 min, >99% pure.

t-Butyl (3,17β-dihydroxyestra-1,3,5(10)-trien-16α-yl) formate (14, E16-1,5neo). Compound 14 was prepared by esterification of acid 8 (85.0 mg, 0.269 mmol) with 2 mL neopentyl alcohol in 10 mL of benzene as described for the preparation of 12. Purification of the residue by flash chromatography on a 2×16 cm column of silica gel using hexanes/EtOAc (3:1) gave 92.3 mg (89%) of 14 as a white solid. Data for 14: TLC, T-5, $R_f$ 0.77. $^1$H NMR (500 MHz, CDCl$_3$) δ 0.86 (s, 3H, H-18), 0.97 (s, 9H, CH$_3$), 3.83 & 3.87 (AB quartet, 2H, J=10.5 Hz, —CH$_2$—), 3.90 (d, 1H, J=8.1 Hz, H-17α), 6.57 (d, 1H, J=2.6 Hz, H-4), 6.63 (dd, 1H, J=8.5, 2.6 Hz, H-2), 7.15 (d, 1H, J=8.5 Hz, H-1); HRMS (ES) calcd for C$_{24}$H$_{38}$NO$_4$ (M+NH$_4^+$) m/e 404.2801, found m/e 404.2809. Anal. (C$_{24}$H$_{34}$O$_4$) C, H. Carbon found 74.44%, calculated 74.58; Hydrogen found 8.91%, calculated 8.87.

Vinyl (3,17β-dihydroxyestran-1,3,5(10)-trien-16α-yl) formates (15, E16-1,2 vin). A solution of 24.4 mg (0.0771 mmol) of acid 8 in 2 mL of vinyl propionate was stirred as 20 μL of a 0.1 M solution of PdCl$_2$—LiCl in vinyl propionate was added. This solution was prepared by combining 17 mg (0.1 mmol) of PdCl$_2$ and 4.2 mg (0.1 mmol) of LiCl in 1 mL MeOH with heating to dissolve, evaporation of the solvent, and resuspension in 1 mL of vinyl propionate. The reaction mixture was stirred at 92° C. for 4 h, poured into CH$_2$Cl$_2$ (50 mL), washed with saturated aqueous NaHCO$_3$ (20 mL) and H$_2$O (20 mL). The organic layer was dried over Na$_2$SO$_4$ and concentrated in vacuo. Purification of the residue by flash chromatography on a 2×17 cm column of silica gel using hexanes/EtOAc (3:1) gave 20 mg (76%) of 15 as a white solid. Purification of 6.5 mg of this material in HPLC system H-7, followed by crystallization from Et$_2$O/hexane gave 4.7 mg of 15 for bioassay. Data for 15: TLC, T-6, $R_f$ 0.57. $^1$H NMR (500 MHz, CDCl$_3$) δ 0.86 (s, 3H, H-18), 3.95 (d, 1H, J=7.7 Hz, H-17α), 4.63 (dd, 1H, J=6.3, 1.6 Hz, vinyl-H), 4.94 (dd, 1H, J=14.0, 1.6 Hz, vinyl-H), 6.57 (d, 1H, J=2.8 Hz, H-4), 6.64 (dd, 1H, J=8.3, 2.8 Hz, H-2), 7.16 (d, 1H, J=8.3 Hz. H-1), 7.33 (dd, 1H, J=14.0, 6.3 Hz, vinyl-H); HRMS (ES) calcd for C$_{21}$H$_{30}$NO$_4$ (M+NH$_4^+$) m/e 360.2175, found m/e 360.2171. HPLC system H-3, 280 nm, $R_t$=12.21 min, and system H-8, 280 nM, $R_t$=11.5 min, >99% pure.

2'-Fluoroethyl (3,17β-dihydroxyestra-1,3,5(10)-trien-16α-yl) formate (16, E16-1,2 F1). Compound 16 was prepared by esterification of acid 8 (15.8 mg, 0.0499 mmol) with 1.5 mL fluoroethanol in 1.5 mL of toluene as described for the preparation of 12. Purification of the residue by flash chromatography on a 2×16 cm column of silica gel using hexanes/EtOAc (2:1) as eluent gave 11.1 mg (59%) of 16 as a white solid. Purification of this material by HPLC in system H-3, followed by crystallization from Et$_2$O/Petroleum ether gave 8.2 mg of 16 for bioassay. Data for 16: TLC, T-6, $R_f$=0.375. $^1$H NMR (500 MHz, CDCl$_3$) δ 0.85 (s, 3H, H-18), 3.91 (d, 1H, J=8.2 Hz, H-17α), 4.36-4.44 (m 2H, CH$_2$CH$_2$F), 4.64 (dt, 2H, J=47.4, 4.2 Hz, CH$_2$CH$_2$F), 6.57 (d, 1H, J=2.8 Hz, H-4), 6.63 (dd, 1H, J=8.3, 2.8 Hz, H-2), 7.16 (d, 1H, J=8.3, H-1); HRMS (ES) calcd for C$_{21}$H$_{31}$FNO$_4$ (M+NH$_4^+$) m/e 380.2237, found m/e 380.2248. HPLC, system H-3, 280 nm, $R_t$=13.0 min, and system H-8, 280 nM, $R_t$=8.5 min, >99% pure.

2',2'-Difluoroethyl (3,17β-dihydroxyestra-1,3,5(10)-trien-16α-yl) formate (17, E16-1,2 F2). Compound 17 was prepared by esterification of acid 8 (25.4 mg, 0.0803 mmol) with 2,2-difluoroethanol as described for the preparation of 16. Purification of this residue by flash chromatography on a 2×17 cm column of silica gel using hexanes/EtOAc (3:1) followed by hexanes/EtOAc (2:1) as eluent gave 29 mg of 17 as a yellow oil. Purification of this material by HPLC with system H-3 gave 22.5 mg (74%) of 17 as a clear colorless oil. Further HPLC purification of 6.2 mg of this material with system H-7, followed by crystallization from Et$_2$O/hexanes gave 5.3 mg of 17 for bioassay. Data for 17: TLC, T-6, $R_f$ 0.5. $^1$H NMR.(500 MHz, CDCl$_3$) δ 0.85 (s, 3H, H-18), 3.91 (d, 1H, J=8.3 Hz, H-17α), 4.32–4.39 (m, 2H, CH$_2$CHF$_2$), 5.99 (tt, 1H, J=55.2, 4.0 Hz, CH$_2$CHF$_2$), 6.57 (d, 1H, J=2.8 Hz, H-4), 6.64 (dd, 1H, J=8.4, 2.8 Hz, H-2), 7.16 (d, 1H, J=8.4 Hz, H-1); HRMS (ES) calc for C$_{21}$H$_{30}$F$_2$NO$_4$ (M+NH$_4^+$) m/e 398.2143, found m/e 398.2148. HPLC system H-3, 280 nm, R$_f$=12.8 min, and system H-8, 280 nM, R$_f$=10.5 min, >99% pure.

2',2',2'-Trifluoroethyl (3,17β-dihydroxyestra-1,3,5(10)-trien-16α-yl) formate (18, E16-1,2 F3). Compound 18 was prepared by esterification of acid 8 (24.9 mg, 0.0787 mmol) with 2,2,2-trifluoroethanol as described for the preparation of 16. Purification of the residue by flash chromatography on a 2×17 cm column of silica gel using hexanes/EtOAc (4:1) as eluent gave 19.1 mg of 18. HPLC purification of this material with system H-3 gave 16.8 mg (54%) of 18 as a slightly yellow oil. Further HPLC purification of 3.1 mg of this material with system H-8, followed by crystallization from Et$_2$O/hexanes gave 1.7 mg of 18 as an amorphous solid. Data for 18: TLC, T-6, R$_f$0.58. $^1$H NMR (500 MHz, CDCl$_3$) δ 0.86 (s, 3H, H-1 8), 3.92 (d, 1H, J=8.3 Hz, H-17α), 4.52–4.58 (m, 2H, CH$_2$CF$_3$), 6.57 (d, 1H, j=3.0 Hz, H-4), 6.64 (dd, 1H, J=8.4, 3.0 Hz, H-2), 7.15 (d, 1H, J=8.4 Hz, H-1); HRMS (ES) calcd for C$_{21}$H$_{29}$F$_3$NO$_4$ (M+NH$_4^+$) m/e 416.2049, found m/e 416.2051. HPLC system H-3, 280 nm, R$_t$=11.6 min, and system H-8, 280 nM, R$_t$=13.5 min, >99% pure.

16α-Hydroxymethylestra-1,3,5(10)-trien-3,17β-diol (19). A solution of 5.3 mg (0.0154 mmol) of ethyl ester 10, 5 mg (0.13 mmol) of LiAlH$_4$ in 1 mL of anhydrous THF was stirred at 0° C. for 1 h under N$_2$. Reaction was quenched with 1 mL of EtOAc, poured into saturated aqueous Na—K tartarate (5 mL) and extracted with EtOAc (3×, 5 mL). Combined organic extracts were dried over Na$_2$SO$_4$ and concentrated in vacuo giving 3.5 mg (75%) of 19 as a white solid TLC, T-5, R$_f$0.51. $^1$H NMR (500 MHz, DMSO-d$_6$+D$_2$O) δ 0.68 (s, 3H, H-18), 3.15 (d, 1H, J=8.1 Hz, H-17α), 3.28 (dd, 1H, J=10.3, 7.1 Hz, CH$_2$OH), 3.51 (dd, 1H, J=10.3, 4.1 Hz, CH$_2$OH), 6.42 (d, 1H, J=2.6 Hz, H-2), 6.49 (dd, 1H, J=8.4, 2.6 Hz, H-2), 7.02 (d, 1H, J=8.4 Hz, H-1); HRMS (ES) calcd for C$_{19}$H$_{26}$O$_3$Na (M+Na$^+$) m/e 325.1780, found m/e 325.1782.

Ethyl (3-benzyloxy-17-oxoestra-1,3,5(10)-trien-16α-yl) acetate (20). A solution of 2.196 g (6.09 mmol) of estrone benzyl ether in 20 mL of anhydrous THF was added in one portion at 0° C. to a solution of 5.79 mmol of LDA (2.89 mL of a 2M solution in heptane, THF, ethylbenzene) in THF (10 mL). The resulting mixture was cooled to −45° C. and a solution of 3.05 g (2.0 mL, 18.3 mmol) of ethyl bromoacetate in 8 mL THF was added dropwise over 5 min. The reaction was stirred at <−20° C. for 7.5 h under N$_2$, poured into H$_2$O (500 mL) and extracted with CH$_2$Cl$_2$ (2×, 300 mL). Combined organic extracts were washed with 10% aqueous sodium metabisulfite, dried over Na$_2$SO$_4$ and concentrated in vacuo giving a yellow oil. Purification of the residue twice by flash chromatography on a 5×17 cm column of silica gel using CH$_2$Cl$_2$ as eluent gave 943.7 mg (35%) of 20 and 954 mg (43%) of recovered starting material. Data for 20: TLC, T-7, R$_f$=0.075. $^1$H NMR (500 MHz, CDCl$_3$) δ 1.00 (s, 3H, H-1 8), 1.29 (t, 3H, J=7.4 Hz, CH$_3$), 4.18 (q, 2H, J=7.4 Hz, CH$_2$), 5.05 (s, 2H, benzylic), 6.74 (d, 1H, J=2.6 Hz, H-4), 6.80 (dd, 1H, J=8.6, 2.6 Hz, H-2), 7.21 (d, 1H, J=8.6 Hz, H-1), 7.31–7.45 (m, 5H, Ar—H); HRMS (ES) Calcd for C$_{29}$H$_{34}$O$_4$Na (M+Na$^+$) m/e 469.2355, found m/e 469.2354.

Ethyl (3-benzyloxy-17β-hydroxyestra-1,3,5(10)-trien-16α-yl) acetate (21). A solution of 50.6 mg (0.113 mmol) of ketone 20, 0.34 mmol of Li(OtBu)$_3$AlH (340 μL of a 1M solution in THF ) in 2 mL of THF was stirred at −78° C. for 5.5 h then at rt for 1 h. Reaction was poured into saturated aqueous NH$_4$Cl (50 mL) and extracted with CH$_2$Cl$_2$ (3×, 50 mL). Combined organic extracts were dried over Na$_2$SO$_4$ and concentrated in vacuo giving a clear colorless oil. Purification of the residue by flash chromatography on a 2×16 cm column of silica gel using CHCl$_3$/EtOAc (5:0.15) gave 36.2 mg (71%) of 21 as a white solid. Data for 21: TLC, T-6, R$_f$0.63. $^1$H NMR (500 MHz, CDCl$_3$) δ 0.85 (s, 3H, H-18), 1.28 (t, 3H, J=7.12 Hz, CH$_3$), 3.35 (d, 1H, J=7.4 Hz, H-17α), 4.16 (q, 2H, J=7.2 Hz, —OCH$_2$—), 6.72 (d, 1H, J=2.5 Hz, H-4), 6.78 (dd, 1H, J=8.8, 2.5 Hz, H-2), 7.21 (d, 1H, J=8.8 Hz, H-1), 7.31–7.44 (m, 5H, Ar—H); HRMS (ES) calcd for C$_{29}$H$_{36}$O$_4$Na (M+Na$^+$) m/e 471.251 1, found 471.2518.

Ethyl (3,17β-dihydroxyestra-1,3,5(10)-trien-16α-yl) acetate (22, E16-2,2). Compound 22 was prepared by hydrogenolysis of 21 (125.2 mg, 0.279 mmol) as described for the preparation of 8. Purification of the residue by flash chromatography on a 2×15 cm column of silica gel using hexanes/EtOAc (2:1) as eluent gave 77.7 mg (78%) of 22. Further purification of 30 mg of this material by HPLC with system H-3 gave 19.9 mg of 22 for bioassay. Data for 22: TLC, T-6, R$_f$0.57. $^1$H NMR (500 MHz, CDCl$_3$) δ 0.85 (s, 3H, H-18), 1.28 (t, 3H, J=7.1 Hz, CH$_3$), 3.38 (d, 1H, J=7.3 Hz, H-17α), 4.16 (q, 2H, J 7.1 Hz, OCH$_2$), 6.56 (d, 1H, J=2.6 Hz, H-4), 6.63 (dd, 1H, J=8.3 Hz, H-2), 7.16 (d, 1H, J=8.3 Hz, H-1). HRMS (ES) calcd for C$_{22}$H$_{34}$NO$_4$ (M+NH$_4^+$) m/e 359.2222, found m/e 359.2232. HPLC system H-3, 280 nm, R$_t$=11.5 min, and system H-9, 280 nm, R$_t$=12 min, >99% pure.

3,17β-Dihydroxyestra-1,3,5(10)-trien-16α-yl acetic acid (23, E16-2,0). Compound 23 was prepared by saponification of ethyl ester 22 (43.3 mg, 0.122 mmol) as described for 7 giving 40 mg (100%). Further purification of 5.9 mg of this material by HPLC with system H-1, followed by acid/base extraction gave 4.8 mg of 23 for bioassay. Data for 23: $^1$H NMR (500 MHz, DMSO) δ 0.70 (s, 3H, H-18), 3.12 (d, 1H, J=7.8 Hz, H-17α), 6.42 (d, 1H, J=2.5 Hz, H-4), 6.49 (dd, 1H, J=8.7, 2.5 Hz, H-2), 7.03 (d, 1H, J=8.7 Hz, H-1), 8.96 (s, 1H, OH). HRMS (ES) calcd for C$_{20}$H$_{30}$NO$_4$ (M+NH$_4^+$) m/e 348.2175, found m/e 348.2188. HPLC system H-1, 280 nm, R$_t$=10 min, and system H-10, 280 nm, R$_t$=12 min, >99% pure.

3-benzyloxy-17β-hydroxyestra-1,3,5(10)-trien-16α-yl acetic acid (24).

Compound 24 was prepared by saponification of ester 21 (106.6 mg, 0.238 mmol) as described for 7 giving 60 mg (60%) of 24 as a white solid. This material was used without further purification in the next step. TLC, T-5, R$_f$0.36.

Methyl-(3-benzyloxy-17β-hydroxyestra-1,3,5(10)-trien-16α-yl) acetate (25). Compound 25 was prepared by esterification of crude 24 (60 mg) with MeOH as described for the preparation of 9. Purification of the residue by flash chromatography on a 2×15 cm column of silica gel using CHCl$_3$/EtOAc (5:0.15) gave 57 mg (92%) of 25 as a white solid. Data for 25: TLC, T-5, R$_f$0.8. $^1$H NMR (500 MHz, CDCl$_3$+D$_2$O) δ 0.85 (s, 3H, H-18), 3.37 (d, 1H, J=7.3 Hz, H-17α), 3.71 (s, 3H, OCH$_3$), 5.04 (s, 2H, benzylic), 6.72 (d, 1H, J=2.8 Hz, H-4), 6.79 (dd, 1H, J=8.5, 2.8 Hz, H-2), 7.21 (d, J=8.5 Hz, H-1), 7.31–7.44 (m, 5H, Ar—H); HRMS (ES) calcd for C$_{28}$H$_{34}$O$_4$Na (M+Na$^+$) m/e 457.2355, found 457.2342.

Methyl 3,17β-dihydroxyestra-1,3,5(10)-trien-16α-yl acetate (26, E16-2,1). Compound 26 was prepared by hydrogenolysis of 25 (54.7 mg, 0.126 mmol) as described for the preparation of 8. Purification of the residue by flash chromatography on a 2×17 cm column of silica using hexanes/EtOAc (2:1) as eluent gave 33.2 mg 26. HPLC purification in 6 portions with system H-3 gave 27.8 mg (64%) of 26 as a white solid. Data for 26: TLC, T-6, $R_f$ 0.456. $^1$H NMR (500 MHz, CDCl$_3$) δ 0.86 (s, 3H, H-18), 3.38 (d, 1H, J=7.3 Hz, H-17α), 3.71 (s, 3H, OCH$_3$), 6.56 (d, 1H, J=2.5 Hz, H-4), 6.63 (dd, 1H, J=8.4, 2.5 Hz, H-2), 7.16 (d, 1H, J=8.4 Hz, H-1). HRMS (ES) calcd for $C_{21}H_{32}NO_4$ (M+NH$_4^+$) m/e 345.2066, found m/e 345.2082. HPLC system H-3, 280 nm, $R_t$=11 min, and system H-11, 280 nm, $R_t$=18 min, >99% pure.

3-Benzyloxy-17β-hydroxyestra-1,3,5(10)-trien-16β-yl acetaldehyde (27). A solution of 10 mg (0.022 mmol) of 21 in anhydrous toluene (200 μL) was stirred at −60° C. as 0.0669 mmol of Dibal (44 μL of a 1.5 M solution in toluene) was added. Reaction was stirred at −60° C. for 2 h, quenched with MeOH (2 mL), poured into H$_2$O (5 mL) and extracted with EtOAc (3×, 5mL). Combined organic extracts were dried over Na$_2$SO$_4$ and concentrated in vacuo. Purification of the residue by flash chromatography on a 2×17 cm column of silica gel using hexanes/EtOAc (1:1) as eluent gave 5.3 mg (59%) of 27 as a clear colorless oil. Data for 27: TLC, T-6, $R_f$ 0.3. $^1$H NMR (500 MHz, CDCl$_3$) δ 0.86 (s, 3H, H-18), 3.33 (d, 1H, J=7.3 Hz, H-17α), 5.04 (s, 3H, benzylic), 6.72 (d, 1H, J=2.5 Hz, H-4), 6.79 (dd, 1H, J=8.8, 2.5 Hz, H-2), 7.21 (d, 1H, J=8.8 Hz, H-1), 7.31–7.44 (m, 5H, Ar—H), 9.83 (s, 1 H, CHO). HRMS (ES) calcd for $C_{27}H_{36}NO_3$ (M+NH$_4^+$) m/e 22.2695, found m/e 422.2681.

16α-Allyl-3-benzyloxyestra-1,3,5(10)-trien-17β-ol (28). A solution of 5.3 mg (0.013 mmol) of 27 in anhydrous toluene (99.7 μL), pyridine (1 μL) and THF (33 μL) was stirred at −78° C. as 0.0156 mmol of Tebbe reagent (31 μL of a 0.5 M solution in toluene) was added by syringe. Reaction was stirred at −78° C. for 2 h, allowed to stir at 40° C. for 2 h then at 0° C. for 1 h. Reaction was quenched with 15% NaOH (25 μL), allowed to stir for ½ h, warmed to rt and passed through a 1" plug of Celite. The filter was washed with EtOAc and the filtrate was concentrated in vacuo. Purification of the residue on a 1×17 cm column of silica gel using hexanes/EtOAc (2:1) followed by hexanes/EtOAc (4:1) gave 1.3 mg (25%) of 28 as a clear colorless oil and 1.8 mg (34%) of recovered 27. Data for 28: TLC, T-6, $R_f$ 0.76. $^1$H NMR (500 MHz, CDCl$_3$) δ 0.83 (s, 3H, H-18), 2.86 (m, 2H, H-6), 3.33 (d, 1H, J=7.4 Hz, H-17α), 5.03–5.12 (m, 2H,=CH$_2$), 5.04 (s, 2H, benzylic), 5.85–5.93 (m, 1H, —CH=CH$_2$), 6.72 d, 1H, J=2.6 Hz, H-4), 6.79 (dd, 1H, J=8.7, 2.6 Hz, H-2), 7.21 (d, 1H, J=8.7 Hz, H-1), 7.31–7.44 (m, 5H, Ar—H).

16α-Allyl-3-benzyloxyestra-1,3,5(10)-trien-17β-yl acetate (29). A solution of 1.874 g (4.65 mmol) of 28$^{25}$, 5.2 mL (55.1 mL) of acetic anhydride in 10.4 mL of anhydrous pyridine was stirred at rt for 16.5 h. Reaction was poured into H$_2$O (300 mL) and extracted with CH$_2$Cl$_2$ (3×, 200 mL). Combined organic extracts were dried over Na$_2$SO$_4$ and concentrated in vacuo. Purification of the residue by flash chromatography on a 3×20 cm column of silica gel using CH$_2$Cl$_2$ as eluent gave 1.73 g (84%) of 29 as a white solid. Data for 29: TLC, T-7, $R_f$ 0.48. $^1$H NMR (500 MHz, CDCl$_3$) δ 0.84 (s, 3H, H-18), 2.07 (s, 3H, Ac), 2.84 (m, 2H, H-6), 4.64 (d, 1H, J=7.3 Hz, H-17α), 4.99–5.07 (m, 2H, =CH$_2$), 5,04 (s, 3H, benzylic), 5.78 (m, 1H, —CH=), 6.72 (d, 1H, J=2.0 Hz, H-4), 6.78 (dd, 1H, J=8.6, 2.0 Hz, H-2), 7.19 (d, 1H, J=8.6 Hz, H-1), 7.31–7.44 (m, 5H, Ar—H).

3-Benzyloxy-16α-(3 '-hydroxypropyl)estra-1,3,5(10)-trien-17β-yl acetate (30). A solution of 629 mg (1.41 mmol) of 29 in anhydrous diglyme (21 mL) was stirred at 0° C. as 1.49 mmol of borane-THF (1.49 mL of a 1 M solution in THF) was added. Reaction was stirred at 0° C. for ½ h the allowed to warm to rt and stir for 2 h. To this was added 660 mg (5.96 mmol) of trimethylamine oxide and reaction was stirred and heated at 150° C. for 2 h, cooled to rt, poured into H$_2$O (150 mL) and extracted with CH$_2$Cl$_2$ (3×, 100 mL). Combined organic extracts were washed with 10% sodium metabisulfite (70 mL), H$_2$O (70 mL), dried over Na$_2$SO$_4$ and concentrated in vacuo. Purification of the residue by flash chromatography on a 3×22 cm column of silica gel using hexanes/EtOAc (1.5:1) as eluent gave 530 mg (81%) of 30 as a white solid. Data for 30: TLC, T-6, $R_f$ 0.34. $^1$H NMR (500 MHz, CDCl$_3$) δ 0.83 (s, 3H, H-18), 2.09 (s, 3H, Oac), 2.85 (m, 2H, H-6), 3.85 (t, 2H, J=5.7 Hz, —CH$_2$O—), 4.63 (d, 1H, J=7.8 Hz, H-17α), 5.04 (s, 2H, benzylic), 6.72 (d, 1H, J=2.6 Hz, H-4), 6.78 (dd, 1H, J=8.2, 2.6 Hz, H-2), 7.19 (d, 1H, J=2.6 Hz, H-1), 7.31–7.44 (m, 5H, Ar—H); HRMS (ES) calcd for $C_{30}H_{38}O_4Na$ (M+Na$^+$) m/e 485.2668, found m/e 485.2679.

3-(3-Benzyloxy-17β-acetoxyestra-1,3,5(10)-trien-16α-yl)propanoic acid (31). Compound 31 was prepared by CrO$_3$ oxidation of 30 (52.9 mg, 1.14 mmol) as described for 6, giving 474 mg of 31 as a white foam: TLC, T-5, $R_f$ 0.64. This material was used without further purification in the next step. HRMS (ES) calcd for $C_{30}H_{36}O_5Na$ (M+Na$^+$) m/e 499.2460, found m/e 499.2449.

3-(3-Benzyloxy-17β-hydroxyestra-1,3,5(10)-trien-16α-yl)propanoic acid (32). Compound 32 was prepared by saponification of crude 31 (474 mg) as described for 7 giving 436 mg of 32 as a white foam: TLC, T-5, $R_f$ 0.54. This material was used without further purification in the next step.

Methyl 3-(3-benzyloxy-17β-hydroxyestra-1,3,5(10)-trien-16α-yl)propanoate (33). Compound 33 was prepared by esterification of crude 32 (436 mg) with MeOH as described for the preparation of 9. Purification of the residue by flash chromatography on a 3×21 cm column of silica gel using hexanes/EtOAc (2:1) as eluent gave 268 mg (52%, three steps) 33 as a white solid. Data for 33: TLC, T-5, $R_f$ 0.76. $^1$H NMR (500 MHz, CDCl$_3$) δ 0.81 (s, 3H, H-1 8), 2.84 (m, 2H, H-6), 3.31 (d, 1H, J=7.3 Hz, H-17α), 3.69 (s, 3H, OCH$_3$), 5.04 (s, 2H, benzylic), 6.72 (d, 1H, J=2.8 Hz, H-4), 6.79 (dd, 1H, J=8.6, 2.8 Hz, H-2), 7.21 (d, 1H, J=8.6 Hz, H-1), 7.31–7.44 (m, 5H, Ar—H); HRMS (ES) calcd for $C_{29}H_{36}O_4Na$ (M+Na$^+$) m/e 471.2511, found m/e 471.2513.

Methyl 3-(3,17β-dihydroxyestra-1,3,5(10)-trien-16α-yl)propanoate (34, E 16-3,1). Compound 34 was prepared by hydrogenolysis of 33 (37.1 mg, 0.0827 mmol) as described for the preparation of 8. Purification of the residue by flash chromatography on a 1×20 cm column of silica gel using hexanes/EtOAc (2:1) as eluent gave 25 mg (84%) of 34. Purification of 20 mg of this material by HPLC with system H-3 gave 17.5 mg of 33 for bioassay. Data for 33: TLC, T-6, $R_f$ 0.45. $^1$H NMR (500 MHz, CDCl$_3$) δ 0.81 (s, 3H, H-18), 3.31 (d, 1H, J=7.4 Hz, H-17α), 3.69 (s, 3H, OCH$_3$), 6.57 (d, 1H, J=2.6 Hz, H-4), 6.63 (dd, 1H, J=8.4, 2.6 Hz, H-2), 7.16 (d, 1H, J=8.4 Hz, H-1). HRMS (ES) calcd for $C_{22}H_{34}NO_4$ (M+NH$_4^+$) m/e 359.2222, found m/e 359.2231. HPLC system H-3, 280 nm, $R_t$=14 min, and system H-12, 280 nM), $R_t$=14.5 min, >99% pure.

3-(3,17β-dihydroxyestra-1,3,5(10)-trien-16α-yl) propanioc acid (35, E16-3,0). Compound 35 was prepared by saponification of 34 (34.8 mg, 0.0971 mmol) as described for 7. Purification of the residue by HPLC in 10 portions with system H-13, gave 19.6 mg (59%) of 35 as a white solid. Data for 35: $^1$H NMR (500 MHz, DMSO) δ 0.68 (s, 3H, H-18), 3.08 (d, 1H, J=7.2 Hz, H-17α), 6.42 (d, 1H, J=2.1 Hz, H-4), 6.49 (dd, 1H, J=8.2, 2.1 Hz, H-2), 7.03 (d, 1H, J=8.2 Hz, H-1), 8.96 (s, 1H, OH). HRMS (ES) calcd for $C_{21}H_{32}NO_4$ (M+$NH_4^+$) m/e 362.2332, found m/e 362.2344. HPLC system H-14, 280 nm, $R_t$=12 min, and system H-13, 280 nm, $R_t$=23 min, >99% pure.

Biological Data

Competitive Binding to the Estrogen Receptor ERα and ERβ. Binding affinities relative to $E_2$ were performed in incubations with the ER in rat uterine cytosol. The ER in uterine cytosol is ERα the classical form of the ER.[38] Female Sprague Dawley rats were castrated and sacrificed 24 h later. The uterus was removed and homogenized in ice-cold TEGDMo buffer (10 mM Tris, 1.5 mM $Na_2$-EDTA, 10% (v/v) glycerol, 1.0 mM dithiothreitol, 25 mM sodium molybdate, pH 7.4 at 4° C.). and centrifuged at 105,000 g for 45 min at 4° C. The supernatant (cytosol) was frozen on dry ice and stored at −80° C. until assay. For assay, the cytosol was defrosted, diluted and incubated with 1 nM [$^3H$]$E_2$ in the presence and absence of non-radioactive $E_2$, estrone ($E_1$) and the $E_2$-carboxy analogs. Incubations were carried out on ice overnight and bound radioactivity was separated from free by adsorption with dextran coated charcoal and quantified by counting.[26] Relative Binding Affinity (RBA) was determined by analysis of the displacement curves by the curve-fitting program Prism (Graph-Pad Software inc., San Diego, Calif.). The results shown in Table 1. below, are from at least 3 separate experiments performed in duplicate. A selected number of $E_2$-16α-alkyl esters were also tested by Dr Paul Shughrue for binding to ERβ. The assay was performed in competition with [$^3H$]$E_2$ in lysates of *Escherichia coli* in which human ERβ is expressed as described, with the exception that the incubation was performed overnight at 0–2° C.[27] The results are shown in Table 1 as the ratio of the RBA of ERα/ERβ in which the binding to ERα was determined in parallel by Dr. Shughrue in the same manner as ERβ, i.e., human ERα expressed in *Escherichia coli*.

Estrogenic Potency in Ishikawa Cells. The estrogenic potency of the $E_2$-analogs was determined in a estrogen bioassay, the induction of AlkP in human endometrial adenocarcinoma cells (Ishikawa) grown in 96-well microtiter plates as we have previously described.[28] In short, the cells are grown in phenol red free medium with estrogen depleted (charcoal stripped) bovine serum in the presence or absence of varying amounts of the steroids. $E_2$ and $E_1$ were included for comparison. After 3 days, the cells are washed, frozen and thawed, and then incubated with 5 mM p-nitrophenyl phosphate, a chromogenic substrate for the AlkP enzyme, at pH 9.8. To ensure linear enzymatic analysis, the plates are monitored kinetically for the for the production of p-nitrophenol at 405 nm. The relative stimulatory activity is determined by analysis of the curve fitting program Prism. Each compound was analyzed in at least 3 separate experiments performed in duplicate.

Figure 2:
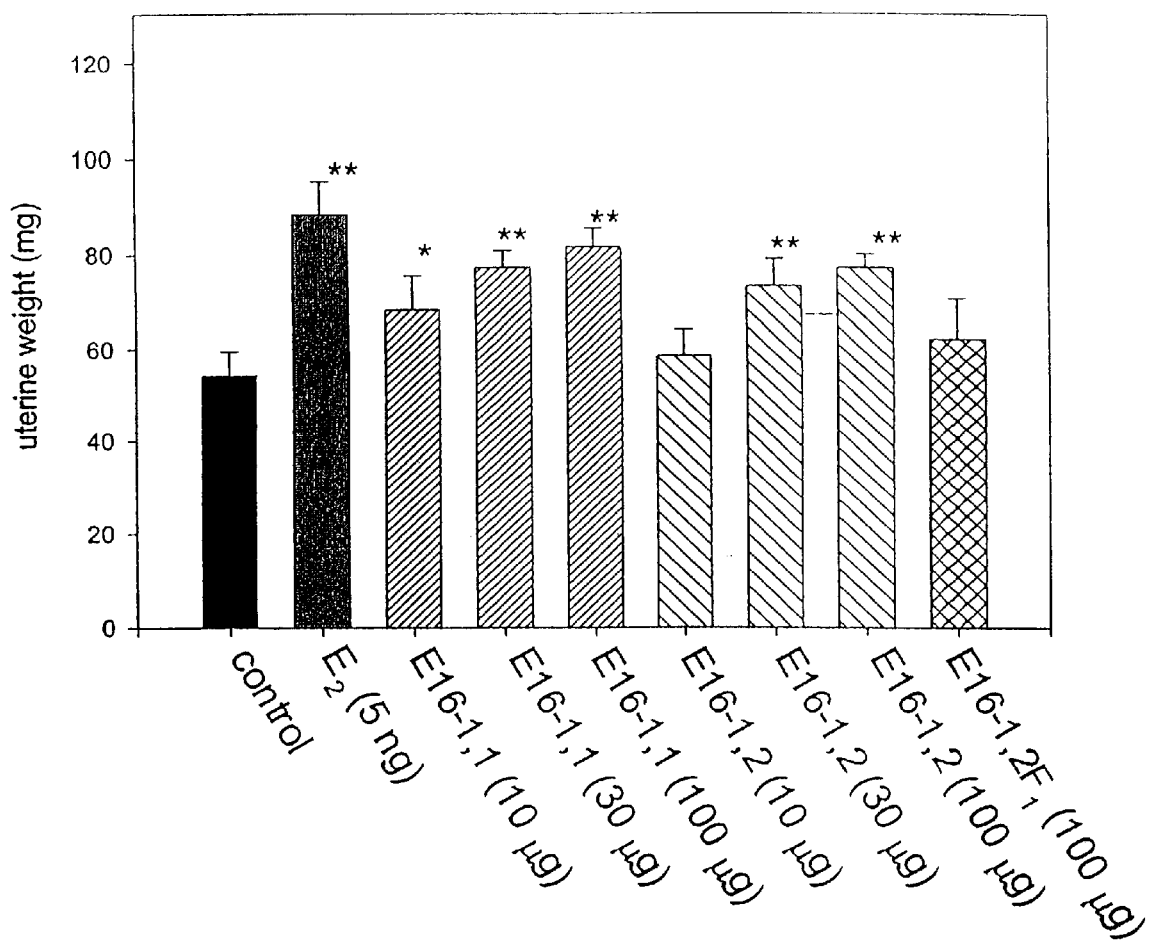
FIG. 2 depicts of the results of an in vivo systemic estrogenic assay (uterotrophic assay) as described in the experimental section. Immature female rats (22 days old) were injected with E16-1,1, E16-1,2 and E16-1,2F1 as well as $E_2$ in sesame oil once daily for 3 days. On the fourth day the animals were killed, the uteri removed and weighed. The total dose is shown. Controls were injected with sesame oil. Error bars are±S.D. n=5. *$P<0.05$, **$P<0.001$ when compared to the control.

In Vivo Estrogen Bioassays: Uterine Weight. Systemic estrogenic potency was determined by a uterotrophic assay in immature rats as described.[33] Female Sprague-Dawley rats, 22 days old, were injected subcutaneously daily for 3 days with an injection volume of 0.1 mL of the 16α-alkyl esters, a total dose of between, 1–300 μg, or E2, 0.001–0.1 μg, in sesame oil. Control animals received sesame oil. On the fourth day, the animals were killed, the uteri were removed, dissected, blotted and weighed. Each compound was assayed in 3 separate experiments with n=5. The results of a typical experiment is shown in FIG. 2.

Figure 3:
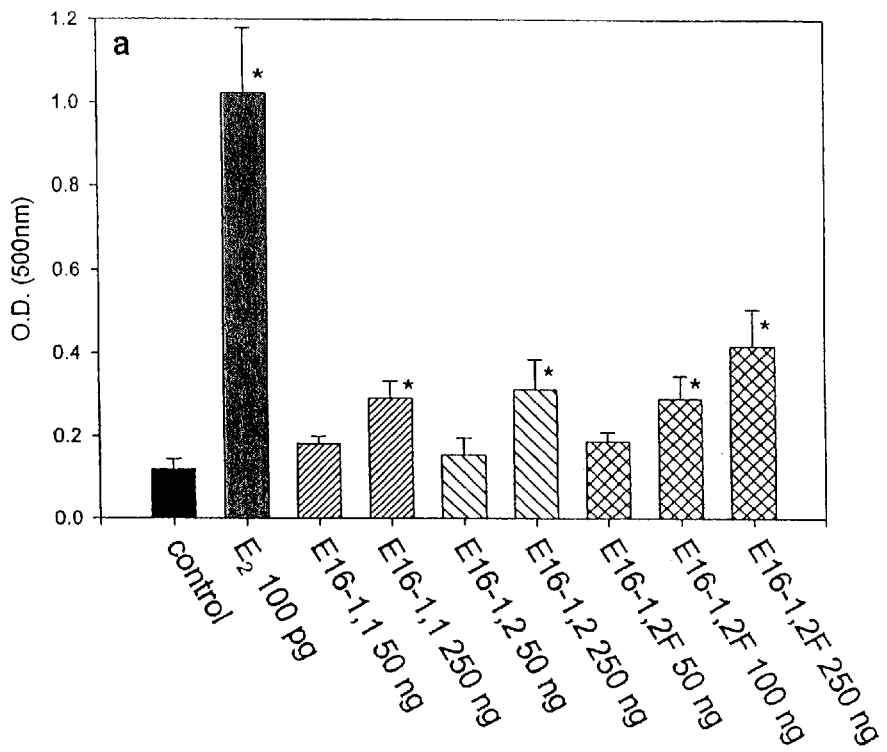
FIG. 3 depicts the results of in vivo local estrogenic assay (vaginal assay). Castrated female mice were intravaginally administered E16-1,1, E16-1,2, E16-1,2$F_1$ and $E_2$ in a single dose.
Figure 3:
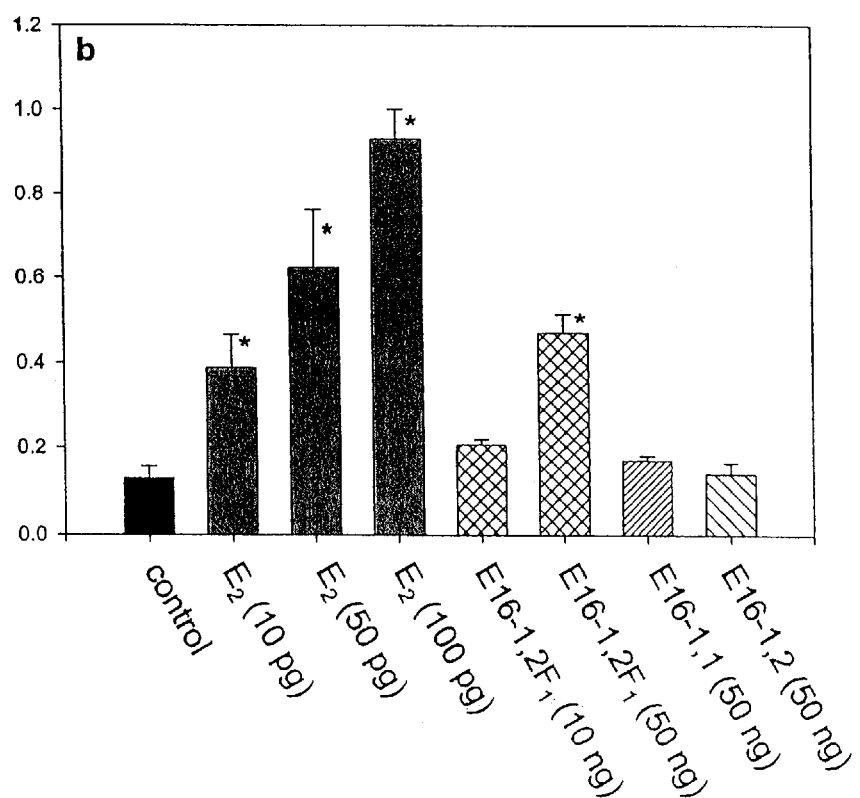

In Vivo Estrogen Bioassays: Vaginal reductases. The estrogenic action of locally applied $E_2$-16α-alkyl esters on the vagina was determined by measuring the induction of vaginal reductases.[34] Female CD-1 mice were ovariectomized and 1 week later were instilled with the $E_2$-16α-alkyl esters or $E_2$ in 10 μL of 25% propylene glycol in saline. In some experiments as indicated, the method was modified by dissolving and injecting the estrogens in 10 μL of sesame oil. The next morning 0.5 mg of 2,3,5-triphenyltetrazolium chloride in 20 μL of saline was instilled in the vagina. Thirty minutes the animals were killed and the vaginas removed, washed thoroughly with saline and then blotted on filter paper. Each vagina was placed in a 12×75 mm test tube and extracted for 1 hour with ethanol/tetrachloroethylene (3:1). Afterwards, the solvent was removed and the formazan product in the organic extract was quantified at 500 nm. Each compound was assayed on at least 3 separate occasions with at least 5 replicates each time. The results of a typical experiment is shown in FIG. 3.

Esterase. Esterase activity was measured in rat hepatic microsomes essentially using the conditions described.[39] Liver obtained from Sprague-Dawley rats was washed with phosphate buffered saline and homogenized in 3 volumes of cold 0.25 M sucrose and centrifuged at 700 g for 10 min and then at 10,000 g for 20 min. The resulting supernatant was centrifuged at 105,000 g for 60 min. The pellet was suspended in 0.1 M phosphate buffer pH 7.4 and washed by centrifugation at 105,000 g for 60 min. The washed pellet was suspended in 0.1 M Tris-HCl pH 8.0 at a concentration of ~13 mg protein/ml and frozen at −80° C. For assay, the pellets were thawed and diluted with the same buffer. The incubation mixture consisted of the microsomal enzyme preparation, 0.28 mg protein/ml, $E_2$-16α-alkyl esters, 50 μM, added in 10 μL of ethanol, all in a final volume of 1 mL of Tris buffer pH 8.0. Since the rates of reaction are widely different for the various esters, the incubation times were varied accordingly to obtain linear kinetics. At several appropriate time points, 100 μL aliquots were withdrawn and the reaction was quenched with 33 μL $CH_3CN$, followed by a 33 μL of a solution of THF containing 1 αg of the internal standard, 6-ketoestradiol. The quenched aliquot was centrifuged for several minutes on bench-top centrifuge and 80 μl of the supernatant was analyzed for the esterase-hydrolysis product (the corresponding $E_2$-16α-carboxylic acid: E16-1,0 8; E16-2,0 23; E16-3,0 35) by reversed phase HPLC with system H-10 for $E_2$-16-1 and E2-16-2 esters, and with system H-15 for E2-16-3 esters. The $E_2$-16α-carboxyl products, ($R_t$ for E16-1,0 8=7 min and for E16-2,0 23=9 min, E16-3,0 35=6.5 min) and the internal standard, 6-ketoestradiol ($R_t$ 7.5 min in system H-10, and 5 min in system H-15) were quantified at 280 nm on the HPLC UV detector. The UV absorbance was converted to moles of product by comparison to standard curves and corrected for recovery of the internal standard, 6-ketoestradiol. The velocity of the reaction for each ester, in nmol product/min/ml/ was then normalized to the ester, E16-1,2 10 and is shown in Table 1 as relative hydrolytic activity (RHA). The enzymatic velocity for the hydrolysis of E16-1,2 10 was 0.9±0.2 (S.D.) nmol product/min/ml over the various experiments. Since all of the esters could not be tested simultaneously, in each case we compared the rate of hydrolysis of the test compound to that of E16-1,2 10 run concurrently. All compounds were tested in triplicate in 3 separate experiments.

The various $E_2$-16α-alkyl esters, including the reactive E16-1,2vin 15, were stable under the conditions used in the esterase assay. Each of the substrates was incubated with heat denatured (1 h at 80° C.) enzyme at 37° C. for periods that exceeded the incubation times of the enzyme assay. Only insignificant amounts of carboxyl products were formed from any of these esters during the incubations with denatured enzyme.

TABLE 1

Estrogenic Properties of $E_2$-16α-alkylesters

| Compound[a] | ER RBA* | ERα/ERβ | Ishikawa Cell AlkP RSA[†] | Esterase RHA[‡] |
|---|---|---|---|---|
| $E_2$ | 100 | — | 100 | — |
| $E_1$ | 30 ± 11 | — | 7 ± 2 | — |
| E16-1,0 | 0 | — | 0 | — |
| E16-1,1 | 35 ± 4 | 750 | 10 ± 3 | 45 ± 10 |
| E16-1,2 | 40 ± 10 | 1,300 | 11 ± 5 | 100 |
| E16-1,3 | 34 ± 9 | — | 2 ± 0 | 230 ± 50 |
| E16-1,3i | 7 ± 4 | — | 0.1 ± 0.06 | 140 ± 10 |
| E16-1,4 | 28 ± 17 | — | 1 ± 0 | 350 ± 50 |
| E16-1,5neo | 14 ± 3 | — | 1 ± 0.6 | 50 ± 5 |
| E16-1,2$F_1$ | 35 ± 3 | 2,000 | 13 ± 5 | 420 ± 40 |
| E16-1,2$F_2$ | 10 ± 3 | 1,800 | 4 ± 1 | 2,350 ± 275 |
| E16-1,2$F_3$ | 7 ± 1 | — | 3 ± 1 | 8,200 ± 1,800 |
| E16-1,2vin | 6 ± 2 | — | 0.4 ± 0.3 | 20,300 ± 5,500 |
| E16-2,0 | 0 | — | 0 | — |
| E16-2,1 | 5 ± 2 | — | 0.5 ± 0.1 | 340 ± 30 |
| E16-2,2 | 5 ± 1 | — | 0.3 ± 0.1 | 700 ± 120 |
| E16-3,0 | 0.1 ± 0.1 | — | 0 | — |
| E16-3,1 | 1 ± 1 | — | 0 | 910 ± 100 |

Figure 1:
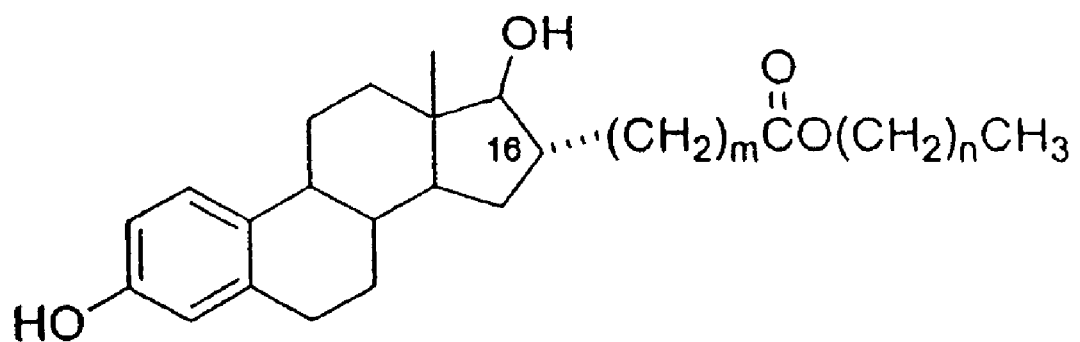
FIG. 1 provides an abbreviation key for the $E_2$-16α-carboxy esters of the present invention. E16-(m+1),(n+1): where 16 is the position in the steroid nucleus from which the ester chain originates and the quantity (m+1) is the number of carbon atoms in the acid and (n+1), the alcohol portion of the chain containing the ester. e.g. E16-2,2; in the figure m and n=1.

[a]Abbreviations are shown in FIG. 1, with examples as follows: E16-1,0 is the formic acid analog of $E_2$. E16-1,1 is the methyl ester of the formate analog etc. 3i is the isopropyl ester, 5neo is the neopentyl ester, and 2vin is the vinyl ester. F is fluorine substitution in the 2'-position of an ethyl ester, i.e. $F_3$ is the 2'2'2'-trifluoroethyl ester. *RBA, relative binding affinity in the rat uterine estrogen receptor (ER) assay where $E_2$ = 100. ERα/ERβ is the ratio of the RBAs ($E_2$ = 100) determined in lysates of *Escherichia coli* in which human ERβ and ERα were separately expressed. [†]RSA, relative stimulatory activity in the induction of alkaline phosphatase (AlkP) activity in the Ishikawa estrogen bioassay where $E_2$ = 100;. [‡]RHA, relative hydrolytic activity in the esterase assay with rat hepatic microsomes in comparison to E16-1,2 = 100. The dash (–) indicates not done. All values are ± S.D.

Results and Discussion

The $E_2$-16α-alkyl carboxylic acid analogs and their esters were tested in a variety of estrogenic assays and an esterase assay to determine their estrogenic potency and the relative rate of their enzymatic hydrolysis. The receptor studies in uterine cytosol (ERα) show a distinct trend (Table 1). None of the parent carboxylic acid analogs, E16-1,0, E16-2,0 and E16-3,0 showed significant binding to the ER. Of those steroid-esters examined, increasing the distance of the ester function from the steroid ring by elongating the alkyl tether dramatically decreases the binding. Thus, in the series of methyl esters, E16-1,1 has a RBA=35%, E16-2,1=5% and E16-3,1=1%. Likewise in the ethyl ester series, E16-1,2 ha RBA=40%, E16-2,2=5%. This precipitous decline with increasing number of carbon atoms did not occur with the alcohol portion of the ester. Here the length of the alcohol portion of the ester had no effect on ER binding: E16-1,1, E16-1,2, E16-1,3 all had RBAs of approximately 35–40%, and E16-1,4 at 28% was not significantly different from the others. Consequently, the pairs (E16-1,2 and E16-2,1) and (E16-1,3 E16-3,1) are all esters with the same number of carbon and oxygen atoms, but their binding to the ER is very different. Noteworthy, all of these E16-1 esters were at least as potent as the natural estrogen, estrone ($E_1$), 30%. However, the E16-1 esters made from bulky alcohols had a markedly decreased affinity for the receptor: the RBA of the neopentyl ester E16-1,5Sneo was 7%, and the isopropyl ester E16-1,3i, 7%. The fluoroethyl ester, E16-1,2$F_1$ was a good ligand, with an RBA of 35% comparable to E16-1,2. Additional fluorine atoms decreased the affinity for the ER: E16-1,2$F_2$ =10% and E16-1,2$F_3$=7%. The vinyl ester, E16-1,2vin also had a RBA of 6%.

A few of the E16-1 esters that had high affinity for ERα were also tested for binding to the ERβ. As can be seen in Table 1, none of these esters bound well to ERβ. The Era to ERβ ratio of their RBAs ranged from 750 for E 16-1,1 to 2,000 for E16-1,2F. This difference in the affinity of the $E_2$-16α-alkyl esters for the 2 ERs had previously been reported that the 16α-substituted ER ligand, 16α-iodoestradiol, which binds with high affinity to the classical ER, ERα[26] binds only poorly to ERβ[27] Apparently, most substituents at C-16α are not accommodated by ERβ although many are transparent to ERα.

All of the $E_2$-16α-alkyl carboxylic acids and their esters were tested for their estrogenic potency by measuring their affect on the induction of alkaline phosphatase (AlkP) in the human endometrial adenocarcinoma cell line Ishikawa. We have previously shown that this assay accurately assesses the potency of a wide variety of estrogenic compounds.[28] As can be seen in Table 1, the potencies determined in this experiment are different than those measured in the ER assay. Three of the esters, E16-1,1, E 16–1,2, and E16-1,2F had fairly high estrogenic potencies (compared to $E_2$) with RSAs of 10, 11 and 13% respectively. They were at least as effective as $E_1$, 7% and probably more so, although the differences were not significant. Contrariwise, several of the esters that had relatively high RBAs in the ER binding assay, including E16-1,3, E16-1,4, had a much lower potency in the Ishikawa cell assay. Most of the other esters also had considerably lower estrogenic action than would have been predicted on the basis of their receptor affinity.

The reason for the discrepancy between ER binding and estrogenic potency became clear when the $E_2$-16α-alkyl esters were tested as substrates for the esterase(s) in rat hepatic microsomes. It can be seen in Table 1 that there are dramatic differences in the velocity of the esterase reaction with the various esters. In general, the longer the alkyl chain, regardless of whether it is in the carboxylic acid or alcohol portion of the ester function, the more rapid the hydrolytic cleavage. This is as expected, for it has been shown that increasing lipophilicity of the alcohol portion of an ester leads to an increased rate of enzymatic cleavage [29] and it is clear that the further removed that the ester function is from the bulky steroid nucleus the more accessible it is to the enzyme. Steric hindrance is also a factor in the hydrolysis of the branched chain alcohols, E16-1,3i, and E16-1,5neo, in which the relative rate of reaction is markedly decreased; with RHA=140 and 50 respectively compared to E16-1,3, RHA=230. The fluorine substituted esters, E16-1,2$F_1$, E16-1,2$F_2$ and E16-1,2$F_3$ showed a large increase in enzymatic hydrolysis that was directly related to the number of fluorine atoms at the 2'-position. The rapid rate of hydrolysis of esters of fluorinated alcohols has been ascribed to the increased acidity of the leaving group alcohol.[30] Likewise, vinyl esters have been shown to be excellent substrates for esterases [31], consistent with the very high rate of cleavage of E16-1,2vin.

In evaluating these compounds, binding to the ER is, of course, the most important factor in the determination of estrogenic potential. However, in these biological systems, additional factors such as catabolism must be weighed. In general, in these experiments, the estrogenic potency of each compound as determined by the stimulation of AlkP in the Ishikawa cells (RSA) is consistent with its binding to the ER (RBA) provided that its susceptibility to esterase cleavage (RHA) is considered. Because the carboxylic acid analogs of $E_2$ are inactive (Table 1), the rate of hydrolysis of the esters is an important factor. This can be seen in the estrogenic potency of the straight-chain $E_2$-16-1 esters, $E_2$-16-1,1 through $E_2$-16-1,4. They all have approximately the same RBA, but their RSA decreases with increasing chain length, which reflects their increasing enzymatic cleavage rates with increasing chain length. The $E_2$-16-2 and $E_2$-16-3 esters have low RBAs and high RHAs, and consequently the potency of all of these compounds is low.

The convergence of binding (RBA) and hydrolysis (RHA) as the determinant of potency (RSA) does not hold as well for the fluorinated esters. As can be seen in Table 1, above, E16-1,2$F_1$, and E16-1,2 have about the same RBA for ER$\alpha$, but since the monofluorinated ester is cleaved at about 4 times the rate of the non-fluorinated ester, it might be assumed that E16-1,2 should be considerably more potent. However, both esters have the same RSA. This also appears to be true for the difluoro and trifluoro ethyl esters. While both of these fluorinated esters have approximately the same RBA as E16-1,3i, their RHA is at least 17 to 60 times greater. If these 2 factors, enzymatic hydrolysis and ER binding are considered, then the isopropyl ester should be the more potent. However, the isopropyl ester is almost inactive, while conversely the difluoro and trifluoro ethyl esters, although weak estrogens, are significantly more active. An explanation for these apparently conflicting findings may be that competitive binding studies which are indirect measurements, do not always accurately reflect the true binding affinity. More likely though, the RBA does not necessarily reflect the ligand induced conformational changes of the receptor which directly affects the transcriptional stimulation of estrogen responsive genes.[32] Thus, receptor stimulation of genes is more complex than is apparent from ligand binding. In any case, the fluorine substituted esters are more potent estrogens than would be predicted on the basis of their RBA and RHA.

Three of estrogen esters, the methyl (E16-1,1), ethyl (E16-1,2) and fluoroethyl (E16-1,2$F_1$) esters of E16-1,0 that were most potent in the Ishikawa assay were tested for their systemic estrogenic activity in the classical in vivo assay, uterotrophic stimulation of the immature rat[33]. In this assay all of the test compounds were administered in sesame oil. Again, $E_2$ included for comparison. As can be seen in FIG. 2, five ng of $E_2$ produced a statistically significant stimulation in the weight of the uterus. As suspected, the systemic potency of the esters was much lower than would be expected on the basis of their action in the Ishikawa cells where their potency (RSA) was at least 10% of $E_2$. The ester with the highest systemic potency, E16-1,1, the methyl ester had a small stimulatory action (P<0.05) at 10 $\mu$g (total dose per animal) in this experiment. In 2 other separate experiments a small effect at this dose was also detected but it was not statistically significant. The ester produced a reproducible and statistically significant stimulation at 30–50 $\mu$g (P<0.01). In the experiment shown in FIG. 2, the stimulation at 30 $\mu$g was approximated as equivalent to that produced by 3 ng of $E_2$. Thus in the systemic assay E16-1,1 had approximately 1/10,000 the potency of $E_2$. Although the response increased at the 100 $\mu$g dose it was not proportional and was equivalent to about 4 $\mu$g of $E_2$, reflecting a 1/25,000 ratio. E16-1,2 produced no measurable stimulation at 10 $\mu$g, and a small increase in uterine weight at 30 $\mu$g. The uterotrophic effect of the 30 and 100 $\mu$g dose of E16-1,2 were approximated as equivalent to 2.5 and 4 $\mu$g of $E_2$ respectively, a relative potency ranging from 1/12,000 to 1/25,000 of E2.

The fluoroethyl ester, E16-1,2$F_1$, was less potent in the systemic assay than either the methyl or ethyl esters. It did not produce a uterotrophic stimulation at 100 $\mu$g. In other experiments (not shown) 300 $\mu$g of E16-1,2$F_1$ produced a small uterotrophic effect, equivalent to less than 5 ng of $E_2$. The uterotrophic activity of the fluoroethyl ester is approximated at less than 1/60,000 of $E_2$. Consequently, these 3 esters which bind to the ER with a RBA of 30 to 40% of $E_2$ and have a stimulatory activity in the Ishikawa cells of about 10% of E2, show only a very weak systemic estrogenic action, ranging from 0.01% to 0.002% of $E_2$. E16-1,2$F_1$ has less systemic activity than the other 2 formyl esters, which is likely caused by its high relative rate of enzymatic hydrolysis to E 16-1,0 (Table 1). In fact, the most likely explanation for the very low activity of the 3 esters is their rapid hydrolysis to the inactive steroid carboxylic acid El6-1,0.

These three esters, E16-1,1, E16-1,2 and E16-1,2$F_1$ were tested to determine whether they were estrogenic in an in vivo assay of local activity, stimulation of vaginal reductase (s) in the ovariectomized mouse. As can be seen in FIG. 3a. all of the esters were estrogenic in this assay, producing a statistically significant (P<0.001) stimulation at the level of 250 ng for the methyl and ethyl esters, and 100 ng for, the monofluoroethyl ester. The potency of the monofluoroethyl ester in this assay was greater than the other 2 esters; the stimulation produced by 100 ng of E16-1,2$F_1$ was equal to 250 ng of E16-1,1 and E16-1,2, and the stimulation produced by 250 ng of E16-1,2$F_1$ was greater than that of 250 ng of E16-1,1 and F16-1,2 (p<0.05). However, the vaginal stimulation induced by the esters was considerably lower than that of $E_2$. In this experiment, as in the original assay[34], the steroids were instilled in the vagina in aqueous propylene glycol. In this aqueous solvent the y are immediately available to the esterase(s) in the vaginal secretions and cells. Consequently, they are rapidly hydrolyzed and have only a short stimulatory period. Since $E_2$ is not susceptible to esterase attack it is metabolized relatively slowly in this paradigm and it has a much longer stimulatory action. This contrasts to the systemic, uterotrophic, assay in which the esters (as well as $E_2$) were injected in an oil, which serves to shield them from metabolism and thus, prolong estrogenic stimulation. Consequently, we repeated the vaginal assay substituting sesame oil instead of the aqueous medium as the vehicle. As can be seen in FIG. 3b, at 50 ng both the methyl and ethyl esters were still not stimulatory but, the 50 ng of the monofluoroethyl ester produced a significant estrogenic effect which was approximated as equivalent to a dose of 20 pg of $E_2$. In this and other experiments there was a consistent stimulation at 10 ng of E16-1,2$F_1$, however, it was not statistically significant. Thus, in the mouse vaginal assay the monofluoroethyl ester E16-1,2$F_1$ had a relative potency of approximately 1/2,500 of $E_2$. The potency of E16-1,2$F_1$ in the vaginal assay relative to $E_2$ is considerably higher than that in the systemic assay (<1/60,000). However, this is probably an underestimation of the potency of the esters in the vaginal assay because the tissues of the mouse have a higher level of non-specific esterase than the rat[35], the species in which the systemic assay was determined. High levels of esterases would lead to a rapid hydrolysis and deactivation of the esters. Regardless, this experiment demonstratess that these labile esters possess significant estrogenic action when administered directly to an estrogen target tissue.

Vaginal creams containing estrogens are well-known forms of pharmacological treatment of vaginal dyspareunia. In addition to $E_2$, other weaker estrogens such as, estriol and $E_1$ have been used in vaginal preparations with the intention of producing a local effect. However, all of these estrogens, when applied vaginally, are adsorbed into the bloodstream and produce systemic effects.[7-10] Those studies concluded that vaginally administered estrogens are therapeutically efficacious but, that their action is not regionally confined and therefore, that they should not be used in patients in whom systemic estrogens are contraindicated. In the present study, we have synthesized a series of steroids substituted at 16α- with carboxylic acid esters as "soft-estrogens". These compounds are rapidly inactivated by hydrolytic esterases in order to confine their activity to the site of application, in this case, the vagina (FIG. 4). We found that 3 of these esters E16-1,1, E16-1,2 and E16-1,2$F_1$ had the desired characteristics osf high ER binding activity and estrogenic potency (Table 1). As required for a "soft-estrogen" the enzymatic hydrolysis product, the parent carboxylic acid E16-1,0, was devoid of these estrogenic activities. Each of the esters exhibited exceedingly low systemic activity (FIG. 2) and yet they were active in the vaginal, local assay. One of these compounds, E16-1,2$F_1$, was hydrolyzed very rapidly and thus, it had the lowest systemic action. Conversely, of the 3 esters, it had the highest vaginal activity indicating its use as a pharmaceutical composition with further testing for the treatment of women with vaginal dyspareunia. Further, these studies support the concept of using steroid-carboxylic acid esters as local estrogens.

References

1) Shlipak, M. G.; Simon, J. A.; Vittinghoff, E.; Lin, F.; Barrett-Connor, E.; Knopp, R. H.; Levy, R. I.; Hulley, S. B. Estrogen and Progestin, Lipoprotein(a), and the Risk of Recurrent Coronary Heart Disease Events After Menopause. *JAMA*. 2000, 283, 1845–1852.
2) Beral, V.; Banks, E.; Reeves, G.; Appleby, P. Use of HRT and the Subsequent Risk of Cancer. *J Epidemiol Biostat*. 1999, 4, 191–210.
3) Banks, E.; Beral, V. Hormone Replacement Therapy for Secondary Prevention of Coronary Heart Disease. *JAMA*. 1999, 281, 794–797.
4) Beral, V.; Hermon, C.; Kay, C.; Hannaford, P.; Darby, S.; Reeves, G. Mortality Associated With Oral Contraceptive Use: 25 Year Follow Up of Cohort of 46 000 Women From Royal College of General Practitioners' Oral Contraception Study. *BMJ*. 1999, 318, 96–100.
5) Sarrel, P. M. Sexuality and Menopause. *Obstetrics and Gynecology*. 1990, 75, 26S-30S.
6) Sarrel, P. M. Sexuality. In *The Menopause*; Studd, J., Whitehead, M. I., Eds.; Blackwell Scientific Publications: London, England, 1988; pp 65–75.
7) Schiff, I.; Tulchinsky, D.; Ryan, K. J. Vaginal Absorption of Estrone and 17α-Estradiol. *Fertility and Sterility*. 1977, 28, 1063–1066.
8) Rigg, L. A.; Hermann, H.; Yen, S. S C. Absorption of Estrogens From Vaginal Creams. *N. Engl. J. Med*. 1978, 298, 195–197.
9) Martin, P. L.; Yen, S.S C.; Burnier, A. M.; Hermann, H. Systemic Absorption and Sustained Effects of Vaginal Estrogen Creams. *JAMA*. 1979, 242, 2699–2700.
10) Schiff, I.; Tulchinsky, D.; Ryan, K. J.; Kadner, S.; Levitz, M. Plasma Estriol and Its Conjugates Following Oral and Vaginal Administration of Estriol to Postmenopausal Women: Correlations With Gonadotropin Levels. *Am.J.Obstet.Gynecol*. 1980, 138, 1137–1141.
11) Hasselquist, M. B.; Goldberg, N.; Schroeter, A.; Spelsberg, T. C. Isolation and Characterization of the Estrogen Receptor in Human Skin. *J.Clin.Endocrinol.Metab*. 1980, 50, 76–82.
12) Punnonen, R.; Lovgren, T.; Kouvonen, I. Demonstration of Estrogen Receptors in the Skin. *J.Endocrinol.Invest*. 1980, 3, 217–221.
13) Uzuka, M.; Nakajima, K.; Ohta, S.; Mori, Y. The Mechanism of Estrogen-Induced Increase in Hyaluronic Acid Biosynthesis, With Special Reference to Estrogen Receptor in the Mouse Skin. *Biochim.Biophys.Acta*. 1980, 627, 199–206.
14) Bodor, N. Designing Safer Drugs Based on the Soft Drug Approach. *Trends Pharmac Sci*. 1982, 3, 53–56.
15) Graffner-Nordberg, M.; Sjodin, K.; Tunek, A.; Hallberg, A. Synthesis and Enzymatic Hydrolysis of Esters, Constituting Simple Models of Soft Drugs. *Chem Pharm Bull (Tokyo)*. 1998, 46, 591–601.
16) Laurent, H.; Gerhards, E.; Wiechert, R. New Biologically Active Pregnan-21-Oic Acid Esters. *J.Steroid.Biochem*. 1975, 6, 185–192.
17) Druzgala, P.; Hochhaus, G.; Bodor, N. Soft Drugs—10. Blanching Activity and Receptor Binding Affinity of a New Type of Glucocorticoid: Loteprednol Etabonate. *J.Steroid Biochem Mol Biol*. 1991, 38, 149–154.
18) Lee, H. J.; Soliman, M. R. I. Anti-Inflammatory Steroids Without Pituitary Adrenal Suppression. *Science*. 1982, 215, 989–991.
19) Bucourt, R.; Vignau, M.; Torelli, V. New Biospecific Adsorbents for the Purification of Estradiol Receptor. *J.Biol.Chem*. 1978, 253, 8221–8228.
20) Fevig, T. L.; Mao, M. K.; Katzenellenbogen, J. A. Estrogen Receptor Binding Tolerance of 16□-Substituted Estradiol Derivatives. *Steroids*. 1988, 51, 471498.
21) Rasmusson, G. H.; Arth, G. E. Selective Oxidations of Hydroxy Steroids. In *Organic Reactions in Steroid Chemistry*; Fried, J., Edwards, J., Eds.; Van Nostrand Reinhold Co.: New York, 1972; pp 222
22) Bjorkquist, D. W.; Bush, R. D.; Ezra, F. S.; Keough, T. Cyclopolymerization and Regioselective Synthesis of Vinyl Itaconates. *J. Org Chem*. 1986, 51, 3196–3201.
23) Noyce, D. S.; Denney, D. B. Steric Effects and Stereochemistry of Lithium Aluminum Hydride Reduction. *J. Am Chem Soc*. 1950, 72, 5743–5745.
24) Vaughan, W. R.; Perry jr, R. The Configuration of Isocamphenilanol. *J. Am Chem Soc*. 1952, 74, 5355–5356.
25) Fevig, T. L.; Katzenellenbogen, J. A. A Short, Stereoselective Route to 16α-(Substituted-Alkyl) Estradiol Derivatives. *J. Org. Chem*. 1987, 52, 247–251.
26) Hochberg, R. B.; Rosner, W. The Interaction of 16□ [$^{125}$I]Iodoestradiol With Estrogen Receptor and Other Binding Proteins. *Proc.Natl.Acad.Sci. USA*. 1980, 77, 328–332.
27) Shughrue, P. J.; Lane, M. V.; Merchenthaler, I. Biologically Active Estrogen Receptor-Beta: Evidence From in Vivo Autoradiographic Studies With Estrogen Receptor Alpha-Knockout Mice. *Endocrinology*. 1999, 140, 2613–2620.
28) Littlefield, B. A.; Gurpide, E.; Markiewicz, L.; McKinley, B.; Hochberg, R. B. A Simple and Sensitive Microtiter Plate Estrogen Bioassay Based on Stimulation of Alkaline Phosphatase in Ishikawa Cells: Estrogenic Action of α$^5$ Adrenal Steroids. *Endocrinology*. 1990, 127, 2757–2762.
29) Pannatier, A.; Testa, B.; Etter, J. Enzymatic Hydrolysis by Mouse Skin Homogenates: Structure-Metabolism Relationships of Para-Nitrobenzoate Esters. *International Journal of Parmaceutics*. 1981, 8,167–174.
30) Barton, P.; Laws, A. P.; Page, M. I. Structure-Activity Relationships in the Esterase-Catalysed Hydrolysis and Transesterification of Esters and Lactones. *J. Chem Soc Perkin Trans* 2. 1994,, 2021–2029.
31) Forró, E.; Lundell, K.; Fulop, F.; Kanerva, L. Preparation of the Stereoisomers of 2-Cyanocycloalkanols by Lipase-Catalysed Acylation. *Tetrahedron: Asymmetry.* 1997, 8, 3095–3099.
32) Katzenellenbogen, J. A.; O'Malley, B. W.; Katzenellenbogen, B. S. Tripartite Steroid Hormone Receptor Pharmacology: Interaction With Multiple Effector Sites As a Basis for the Cell- and Promoter-Specific Action of These Hormones. *Molecular Endocrinology.* 1996, 10, 119–131.
33) Emmens, C. W. Estrogens. In Methods in Hormone Research; Dorfinan, R. I., Ed.; Academic Press Inc.: New York, 1962; pp 59–111.
34) Martin, L. The Use of 2-3-5-Triphenyltetrazolium Chloride in the Biological Assay of Oestrogens. *J.Endocrin.* 1960, 20, 187–197.
35) Lund-Pero, M.; Jeppson, B.; Ameklo-Nobin, B.; Sjogren, H.-O.; Holmgren, K.; Pero, R. W. Nonspecific Steroidal Esterase Activity and Distribution in Human and Other Mammalian Tissues. *Clinica Chimica Acta.* 1994, 224, 9–20.
36) Still, C. W.; Kahn, M.; Mitra, A. Rapid Chromatographic Technique for Preparative Separations With Moderate Resolution. *J.Org.Chem.* 1978, 43, 2923–2925.
37) Fried J and Edwards JAEds. *Organic Reactions in Steriod Chemistry*; Van Nostrand Reinhold Co.: New York, 1972; pp 314
38) Kuiper, G. G.; Carlsson, B.; Grandien, K.; Enmark, E.; Haggblad, J.; Nilsson, S.; Gustafsson, J. A. Comparison of the Ligand Binding Specificity and Transcript Tissue Distribution of Estrogen Receptors Alpha and Beta. *Endocrinology.* 1997, 138, 863–870.
39) Schottler, C.; Krisch, K. Hydrolysis of Steroid Hormone Esters by an Unspecific Carboxylesterase From Pig Liver Microsomes. *Biochem.Pharmacol.* 1974, 23, 2867–2875.

What is claimed is:

1. A compound according to the structure:

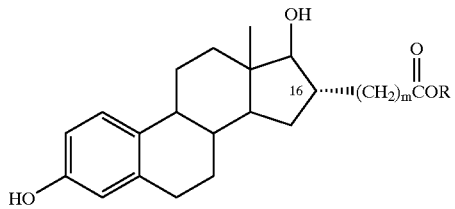

Where R is H, a $C_1$ to $C_5$ alkyl group, vinyl, $CF_3$, $CH_2CH_2F$, $CH_2CHF_2$ and $CH_2CF_3$; and m is from 0–2.

2. The compound according to claim 1 wherein R is methyl, ethyl, propyl, iso-propyl, butyl, iso-butyl, pentyl, neo-pentyl, vinyl, $CF_3$, $CH_2CH_2F$, $CH_2CHF_2$ or $CH_2CF_3$ and m is 0.

3. The compound according to claim 1 wherein m is 0 and R is methyl, ethyl, $CH_2CH_2F$, $CH_2CHF_2$ or $CH_2CF_3$.

4. The compound according to claim 3 wherein R is methyl.

5. The compound according to claim 3 wherein R is ethyl.

6. The compound according to claim 3 wherein R is $CH_2CH_2F$.

7. The compound according to claim 3 wherein R is $CH_2CHF_2$.

8. The compound according to claim 3 wherein R is $CH_2CF_3$.

9. A pharmaceutical composition comprising an effective amount of a compound for alleviating the symptomology of menopause in a patient, said compound having the structure

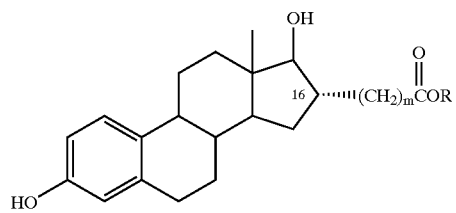

Where R is a $C_1$ to $C_5$ alkyl group, vinyl, $CF_3$, $CH_2CH_2F$, $CH_2CHF_2$ or $CH_2CF_3$ group; and m is from 0–2, optionally in combination with a pharmaceutically acceptable carrier, excipient or additive.

10. The composition according to claim 8 wherein R is methyl, ethyl, propyl, iso-propyl, butyl, iso-butyl, pentyl, neo-pentyl, vinyl, $CF_3$, $CH_2CH_2F$, $CH_2CHF_2$ or $CH_2CF_3$ and m is 0.

11. The composition according to claim 10 wherein m is 0 and R is methyl, ethyl, $CH_2CH_2F$, $CH_2CHF_2$ or $CH_2CF_3$.

12. The composition according to claim 10 wherein R is methyl.

13. The composition according to claim 10 wherein R is ethyl.

14. The composition according to claim 10 wherein R is $CH_2CH_2F$.

15. The composition according to claim 10 wherein R is $CH_2CHF_2$.

16. The composition according to claim 10 wherein R is $CH_2CF_3$.

17. The composition according to claim 10 in topical dosage form.

18. The composition according to claim 10 formulated as a vaginal cream, gel, lotion or suppository.

19. A method for alleviating the symptoms of menopause, comprising administering to a patient in need of therapy a pharmaceutical composition comprising an effective amount of a compound according to the structure:

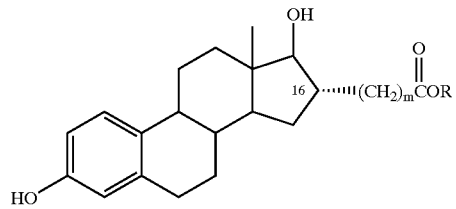

Where R is a $C_1$ to $C_5$ alkyl group, vinyl, $CF_3$, $CH_2CH_2F$, $CH_2CHF_2$ or $CH_2CF_3$ group; and m is from 0–2, optionally in combination with a pharmaceutically acceptable carrier, excipient or additive.

20. The method according to claim 19 wherein said symptom of menopause is selected from the group consisting of bone loss associated with osteoporosis and vaginal dyspareunia.

21. The method according to claim 17 wherein said symptom of menopause is vaginal dyspareunia and said composition is administered to the patient's vaginal membranes.

22. The method according to claim 21 wherein R is methyl.

23. The method according to claim 21 wherein R is ethyl.

24. The method according to claim 21 wherein R is $CH_2CH_2F$.

25. The method according to claim 21 wherein R is $CH_2CHF_2$.

26. The method according to claim 21 wherein R is $CH_2CF_3$.

27. The method according to claim 21 wherein said composition is administered as a vaginal cream, gel, lotion or suppository.

28. The method according to claim 19 wherein said composition is administered within the patient's body from an implant.

29. The method according to claim 20 wherein said symptom of menopause is bone loss associated with osteoporosis and said composition is administered within the patient's body from an implant.

* * * * *

UNITED STATES PATENT AND TRADEMARK OFFICE
CERTIFICATE OF CORRECTION

PATENT NO. : 6,476,012 B2  
APPLICATION NO. : 10/056635  
DATED : November 5, 2002  
INVENTOR(S) : Richard B. Hochberg Page 1 of 1

It is certified that error appears in the above-identified patent and that said Letters Patent is hereby corrected as shown below:

In the Specification

Column 1 Line 7:
After the paragraph under Related Applications, insert the following header and paragraph:
--Grant Support
This invention was made with government support under CA037799 awarded by National Institutes of Health. The government has certain rights in the invention.--

Signed and Sealed this
Twenty-fifth Day of August, 2020

Andrei Iancu
*Director of the United States Patent and Trademark Office*